United States Patent
Mehta et al.

(10) Patent No.: US 9,533,022 B2
(45) Date of Patent: *Jan. 3, 2017

(54) PEPTIDE ANALOGS FOR TREATING DISEASES AND DISORDERS

(71) Applicants: Nozer M. Mehta, Randolph, NJ (US); William Stern, Tenafly, NJ (US); Amy M. Sturmer, Towaco, NJ (US); Morten Asser Karsdal, Kobenhavn (DK); Kim Henriksen, Hillerod (DK)

(72) Inventors: Nozer M. Mehta, Randolph, NJ (US); William Stern, Tenafly, NJ (US); Amy M. Sturmer, Towaco, NJ (US); Morten Asser Karsdal, Kobenhavn (DK); Kim Henriksen, Hillerod (DK)

(73) Assignee: KeyBioscience A/S, Stans (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/634,188

(22) Filed: Feb. 27, 2015

(65) Prior Publication Data

US 2015/0196617 A1 Jul. 16, 2015

Related U.S. Application Data

(63) Continuation-in-part of application No. 13/667,578, filed on Nov. 2, 2012, now Pat. No. 9,006,172.

(60) Provisional application No. 61/578,620, filed on Dec. 21, 2011, provisional application No. 61/554,771, filed on Nov. 2, 2011.

(51) Int. Cl.
| | |
|---|---|
| A61K 38/00 | (2006.01) |
| A61K 38/23 | (2006.01) |
| A61P 3/04 | (2006.01) |
| C07K 5/00 | (2006.01) |
| A61K 38/16 | (2006.01) |
| A61K 31/155 | (2006.01) |
| C07K 14/585 | (2006.01) |

(52) U.S. Cl.
CPC ............ *A61K 38/16* (2013.01); *A61K 31/155* (2013.01); *A61K 38/23* (2013.01); *C07K 14/585* (2013.01)

(58) Field of Classification Search
None
See application file for complete search history.

(56) References Cited

U.S. PATENT DOCUMENTS

| | | | |
|---|---|---|---|
| 4,764,589 A | 8/1988 | Orlowski | |
| 9,006,172 B2 * | 4/2015 | Mehta | A61K 38/23 514/1.1 |
| 2002/0065255 A1 * | 5/2002 | Bay | A61K 47/183 514/166 |
| 2010/0311650 A1 * | 12/2010 | Mehta | C07K 14/00 514/4.9 |

FOREIGN PATENT DOCUMENTS

WO  2010085700 A2  7/2010

OTHER PUBLICATIONS

Lee et al., "Metformin Decreases Food Consumption and Induces Weight Loss in Subjects with Obesity with Type I1 Non-Insulin-Dependent Diabetes," Obes. Res. 6:47-53 (1998).*
Feigh et al., "A novel oral form of salmon calcitonin improves glucose homeostasis and reduces body weight in diet-induced obese rats" Diab. Obesity Metab. 13:911-920 (2011).*
Unigene Laboratories Inc. Unigene Laboratories Inc. Corporate Overview 2010, URL: www.getfillings.com/sec-filings/100325/UNIGENE-LABORATORIES-INC_8-K/dex991.htm, whole document.
Andreassen, et al. Oral formulation of UGP 302, a novel amylin and calcitonin dual receptor agonist, exerts anti-obesity effects in diet-induced obese (DIO) rats, Diabetologia 2013, vol. 56(Suppl1), p. S344, Abstract 867.
Feigh, et al. A novel oral dual-action amylin and calcitonin receptor agonist (UGP 302) rebalances insulin and glucagon hyperglycaemia in Zucker diabetic fatty rats, Diabetologia 2013, vol. 56(Suppl2), p. S405-S406, Abstract 1009.

* cited by examiner

*Primary Examiner* — Julie Ha
*Assistant Examiner* — Kristina M Hellman
(74) *Attorney, Agent, or Firm* — Benjamin Aaron Adler

(57) ABSTRACT

Provided herein are methods for the treatment of type I diabetes, Type II diabetes, metabolic syndrome, or obesity, or of appetite suppression, or for mitigating insulin resistance, or for reducing an undesirably high fasting serum glucose level, or for reducing an undesirably high peak serum glucose level, or for reducing an undesirably high peak serum insulin level, or for reducing an undesirably large response to a glucose tolerance test in synergistic combination with metformin. Treatment is effected with a combination therapy of metformin and a peptide with a sequence selected from SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 19, SEQ ID NO: 20, SEQ ID NO: 21, SEQ ID NO: 22, SEQ ID NO: 23, and SEQ ID NO: 24 administered to a patient.

22 Claims, 25 Drawing Sheets

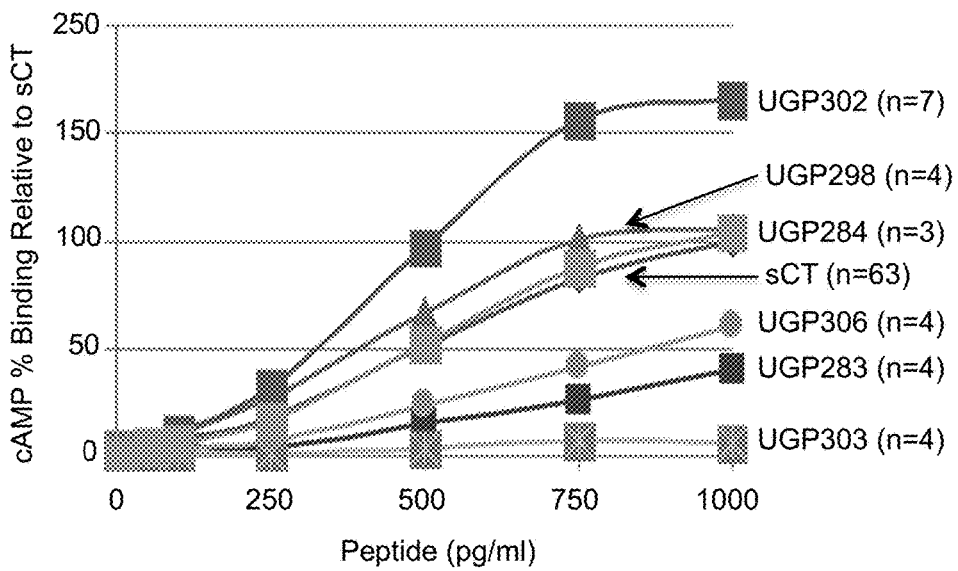
FIG. 11
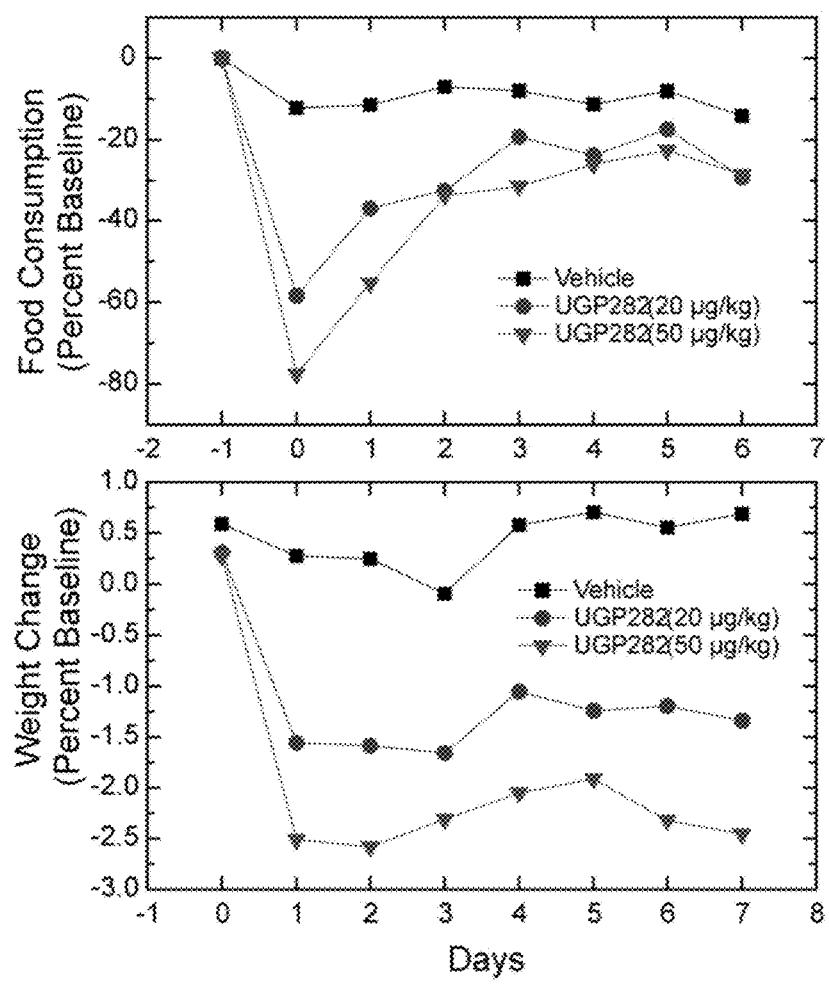
FIG. 12A
FIG. 12B

1

PEPTIDE ANALOGS FOR TREATING DISEASES AND DISORDERS

CROSS-REFERENCE TO RELATED APPLICATIONS

This application is a continuation-in-part under 35 U.S.C. §120 of non-provisional application U.S. Ser. No. 13/667,578, filed Nov. 2, 2012, which claims benefit of priority under 35 U.S.C. §119(e) to provisional application U.S. Ser. No. 61/578,620, filed Dec. 21, 2011, and to provisional application U.S. Ser. No. 61/554,771, filed Nov. 2, 2011, the entirety of all of which are hereby incorporated herein by reference.

BACKGROUND OF THE INVENTION

Field of the Invention

The embodiments disclosed herein relate to mimetics of calcitonin, and more particularly to their use in the treatment of various diseases and disorders, including, but not limited to diabetes (Type I and Type II), excess bodyweight, excessive food consumption and metabolic syndrome, the regulation of blood glucose levels, the regulation of response to glucose tolerance tests, the regulation of food intake, the treatment of osteoporosis and the treatment of osteoarthritis.

Description of the Related Art

Worldwide, there are about 250 million diabetics and the number is projected to double in the next two decades. Over 90% of this population suffers from type 2 diabetes mellitus (T2DM). It is estimated that only 50-60% of persons affected with T2DM or in stages preceding overt T2DM are currently diagnosed. T2DM is a heterogeneous disease characterized by abnormalities in carbohydrate and fat metabolism. The causes of T2DM are multi-factorial and include both genetic and environmental elements that affect β-cell function and insulin sensitivity in tissues such as muscle, liver, pancreas and adipose tissue. As a consequence impaired insulin secretion is observed and paralleled by a progressive decline in β-cell function and chronic insulin resistance. The inability of the endocrine pancreas to compensate for peripheral insulin resistance leads to hyperglycaemia and onset of clinical diabetes. Tissue resistance to insulin-mediated glucose uptake is now recognized as a major pathophysiologic determinant of T2DM. Type I diabetes is characterised by a loss of the ability to produce insulin in response to food intake and hence an inability to regulate blood glucose to a normal physiological level.

A successful criterion for an optimal T2DM intervention is the lowering of blood glucose levels, which can be both chronic lowering of blood glucose levels and increased ability to tolerate high glucose levels after food intake, described by lower peak glucose levels and faster clearance. Both of these situations exert less strain on β-cell insulin output and function.

The physical structure of bone may be compromised by a variety of factors, including disease and injury. One of the most common bone diseases is osteoporosis, which is characterized by low bone mass and structural deterioration of bone tissue, leading to bone fragility and an increased susceptibility to fractures, particularly of the hip, spine and wrist. Osteoporosis develops when there is an imbalance such that the rate of bone resorption exceeds the rate of bone formation. Administering an effective amount of an anti-resorptive agent, such as calcitonin, has shown to prevent resorption of bone.

Inflammatory or degenerative diseases, including diseases of the joints, e.g. osteoarthritis (OA), rheumatoid arthritis (RA) or juvenile rheumatoid arthritis (JRA), and including inflammation that results from autoimmune response, e.g. lupus, ankylosing spondylitis (AS) or multiple sclerosis (MS), can lead to substantial loss of mobility due to pain and joint destruction. Cartilage that covers and cushions bone within joints may become degraded over time thus undesirably permitting direct contact of two bones that can limit motion of one bone relative to the other and/or cause damage to one by the other during motion of the joint. Subchondral bone just beneath the cartilage may also degrade. Administering an effective amount of an anti-resorptive agent, such as calcitonin, may prevent resorption of bone.

SUMMARY OF THE INVENTION

Calcitonin mimetics are disclosed herein.

According to aspects illustrated herein, there is disclosed a peptide having a sequence selected from SEQ ID NO: 11, SEQ ID NO: 12, SEQ ID NO: 13, SEQ ID NO: 14, SEQ ID NO: 15, SEQ ID NO: 17 and SEQ ID NO: 18.

According to aspects illustrated herein, there is disclosed a method that includes administering to a patient an effective amount of a peptide selected from the group consisting of: SEQ ID NO: 11, SEQ ID NO: 12, SEQ ID NO: 13, SEQ ID NO: 14, SEQ ID NO: 15, and SEQ ID NO: 17 to affect a weight reduction in the patient.

According to aspects illustrated herein, there is disclosed a method that includes administering to a patient an effective amount of a peptide selected from the group consisting of: SEQ ID NO: 11, SEQ ID NO: 12, SEQ ID NO: 13, SEQ ID NO: 14, SEQ ID NO: 15, and SEQ ID NO: 17 to affect postprandial glycemic control in the patient.

According to aspects illustrated herein, there is disclosed a method that includes administering to a patient an effective amount of a peptide selected from the group consisting of: SEQ ID NO: 11, SEQ ID NO: 12, SEQ ID NO: 13, SEQ ID NO: 14, SEQ ID NO: 15, and SEQ ID NO: 17 to affect an improvement in glycemic control in the patient.

According to aspects illustrated herein, there is disclosed a method that includes administering to a patient an effective amount of a peptide of SEQ ID NO: 18 having the sequence $C_mSNLSTCVLGKLSQELHKLQTYPRTDVGANXaaXaa_a$ so as to reduce at least one of bone resorption and cartilage degradation in the patient.

According to aspects illustrated herein, there is disclosed a method for the treatment of type I diabetes, Type II diabetes, metabolic syndrome, or obesity, or of appetite suppression, or for mitigating insulin resistance, or for reducing an undesirably high fasting serum glucose level, or for reducing an undesirably high peak serum glucose level, or for reducing an undesirably high peak serum insulin level, or for reducing an undesirably large response to a glucose tolerance test comprising administering to a patient as a combination therapy an effective amount metformin and of a peptide of SEQ ID NOS: 11-24. It has been found that the subject peptides show a synergistic activity when administered in combination with metformin.

BRIEF DESCRIPTION OF THE DRAWINGS

The presently disclosed embodiments will be further explained with reference to the attached drawings, which illustrate the principles thereof.

FIG. 11 shows binding results for six UGP compounds to T47D cell calcitonin receptors as measured in Example 4.

FIG. 12A and FIG. 12B show food consumption (FIG. 12A) and weight change measurements (FIG. 12B) for UGP 282 as measured in Example 5.

Figure 1A:
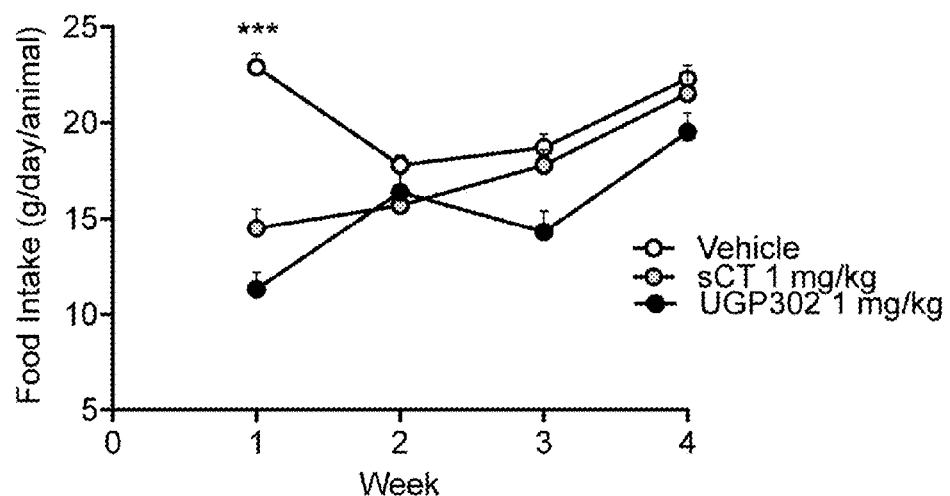
FIG. 1A, FIG. 1B, FIG. 1C, and FIG. 1D show the effect of chronic oral salmon calcitonin ("sCT") versus oral UGP 302 administration food intake (FIG. 1A), on body weight (FIG. 1B), cumulative food intake (FIG. 1C), and change in body weight (FIG. 1D) in DIO rats as measured in Example 1.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF THE INVENTION

Calcitonins are highly conserved over a wide range of species. Full-length native calcitonin is 32 amino acids in length. The sequences of examples of calcitonins are set out below:

```
Salmon
                                    SEQ ID NO: 1
CSNLSTCVLGKLSQELHKLQTYPRTNTGSGTP Mouse
                                    SEQ ID NO: 2
CGNLSTCMLGTYTQDLNKFHTFPQTSIGVEAP Chicken
                                    SEQ ID NO: 3
CASLSTCVLGKLSQELHKLQTYPRTDVGAGTP Eel
                                    SEQ ID NO: 4
CSNLSTCVLGKLSQELHKLQTYPRTDVGAGTP Rat
                                    SEQ ID NO: 5
CGNLSTCMLGTYTQDLNKFHTFPQTSIGVGAP Horse
                                    SEQ ID NO: 6
CSNLSTCVLGTYTQDLNKFHTFPQTAIGVGAP Canine-1
                                    SEQ ID NO: 7
CSNLSTCVLGTYSKDLNNFHTFSGIGFGAETP Canine-2
                                    SEQ ID NO: 8
CSNLSTCVLGTYTQDLNKFHTFPQTAIGVGAP Porcine
                                    SEQ ID NO: 9
CSNLSTCVLSAYWRNLNNFHRFSGMGFGPETP Human
                                    SEQ ID NO: 10
CGNLSTCMLGTYTQDFNKFHTFPQTAIGVGAP
```

Embodiments of the present disclosure relate to calcitonin mimetics. The amino acid sequence of the calcitonin mimetics of the present disclosure are found in Table 1A below.

TABLE 1A

| Calcitonin Mimetic (CM) | Amino Acid Sequence | SEQ ID NO: |
|---|---|---|
| UGP281 | AcCSNLSTCVLGKLSQELHKLQTY PRTDVGANTY-NH$_2$ | 11 |

TABLE 1A-continued

| Calcitonin Mimetic (CM) | Amino Acid Sequence | SEQ ID NO: |
|---|---|---|
| UGP283 | AcCSNLSTCVLGRLSQELHRLQTFPRTDVGANTAcY | 12 |
| UGP284 | PrCSNLSTCVLGKLSQELHKLQTYPRTNTGSGTP-NH$_2$ | 13 |
| UGP298 | SuccCSNLSTCVLGKLSQELHKLQTYPRTNTGSGTP-NH$_2$ | 14 |
| UGP302 | AcCSNLSTCVLGKLSQELHKLQTYPRTDVGANAP-NH$_2$ | 15 |
| UGP303 | KCSNLSTCVLGKLSQELHKLQTYPRTDVGANTY-NH$_2$ | 16 |
| UGP306 | SuccCSNLSTCVLGKLSQELHKLQTYPRTDVGANAY-NH$_2$ | 17 |
| UGP1000 | C$_m$SNLSTCVLGKLSQELHKLQTYPRTDVGANXaaXaa$_a$ | 18 |

In some embodiments, the cysteine at position 1 of the calcitonin mimetics discussed supra is modified ("C$_m$") to reduce the positive charge of the first amino acid. For example, an acetyl group (SEQ ID NOs: 11, 12 and 15), propionyl group (SEQ ID NO: 13), or succinyl group (SEQ ID NOs: 14 and 17) may be substituted on cysteine-1. In some embodiments, the amino acid at the last position ("Xaa$_a$") (position 32 in SEQ ID Nos: 11, 13-15 and 17-18 or position 33 in SEQ ID NO: 16) may include an amidated group "NH$_2$". Alternative ways of reducing positive charge include, but are not limited to, polyethylene glycol-based PEGylation, or the addition of another amino acid such as glutamic acid or aspartic acid at the N-terminus. Alternatively, other amino acids may be added to the N-terminus of peptides discussed supra including, but not limited to, lysine, glycine, formylglycine, leucine, alanine, acetyl alanine, and dialanyl. An example of an amino acid added to the N-terminus of peptides includes SEQ ID NO:16, where a lysine has been added.

"Xaa" in SEQ ID NO: 18 in Table 1 can be any naturally occurring amino acid. In an embodiment Xaa at position 31 is selected from one of threonine or alanine. In an embodiment Xaa at position 32 is selected from one of tyrosine or proline. Thus, SEQ ID NOs: 11, 15, 16 and 17, are encompassed by SEQ ID NO: 18.

Other amino acid sequences of the calcitonin mimetics of the present disclosure are found in Table 1B below. In these sequences the R substituent may be an acylation moiety or may be absent.

TABLE 1B

| Amino Acid Sequence | SEQ ID NO: |
|---|---|
| R-CSNLSTCVLGKLSQELHKLQTYPRTDVGANAP-NH$_2$ | 19 |
| R-CSNLSTCVLGKLSQELHKLQTYPRTNTGSGTP-NH$_2$ | 20 |
| R-CSNLSTCVLGKLSQELHKLQTYPRTDVGANTY-NH$_2$ | 21 |
| R-CSNLSTCVLGRLSQELHRLQTFPRTDVGANTAcY | 22 |
| R-KCSNLSTCVLGKLSQELHKLQTYPRTDVGANTY-NH$_2$ | 23 |
| R-CSNLSTCVLGKLSQELHKLQTYPRTDVGANAY-NH$_2$ | 24 |

As those of skill in the art will appreciate, peptides having a plurality of cysteine residues frequently form a disulfide bridge between two such cysteine residues. All such peptides set forth herein are defined as optionally including one or more such disulfide bridges. While calcitonin mimetics of the present disclosure may exist in free acid form, it is preferred that the C-terminal amino acid be amidated. Applicants expect that such amidation may contribute to the effectiveness and/or bioavailability of the peptide. A preferred technique for manufacturing amidated versions of the calcitonin mimetics of the present disclosure is to react precursors (having glycine in place of the C-terminal amino group of the desired amidated product) in the presence of peptidylglycine alpha-amidating monooxygenase in accordance with known techniques wherein the precursors are converted to amidated products in reactions described, for example, in U.S. Pat. No. 4,708,934 and European Patent Publication Nos. 0 308 067 and 0 382 403. Recombinant production is preferred for both the precursor and the enzyme that catalyzes the conversion of the precursor to salmon calcitonin. Such recombinant production is discussed in Biotechnology, Vol. 11 (1993) pp. 64-70, which further describes a conversion of a precursor to an amidated product. The recombinant product reported there is identical to natural salmon calcitonin, and to salmon calcitonin produced using solution and solid phase chemical peptide synthesis. Production of amidated products may also be accomplished using the process and amidating enzyme set forth by Consalvo, et al. in U.S. Pat. No. 7,445,911; Miller et al., U.S. Patent Publication No. 2006/0292672; Ray et al. 2002, *Protein Expression and Purification*, 26:249-259; and Mehta, 2004, *Biopharm. International*, July, pp. 44-46.

The production of the preferred amidated peptides may proceed, for example, by producing glycine-extended precursor in *E. coli* as a soluble fusion protein with glutathione-S-transferase, or by direct expression of the precursor in accordance with the technique described in U.S. Pat. No. 6,103,495. Such a glycine extended precursor has a molecular structure that is identical to the desired amidated product except at the C-terminus (where the product terminates —X—NH$_2$, while the precursor terminates —X-gly, X being the C-terminal amino acid residue of the product). An alpha-amidating enzyme described in the publications above catalyzes conversion of precursors to product. That enzyme is preferably recombinantly produced, for example, in Chinese Hamster Ovary (CHO) cells), as described in the Biotechnology and Biopharm. articles cited above.

Free acid forms of peptide active agents of the present disclosure may be produced in like manner, except without including a C-terminal glycine on the "precursor", which precursor is instead the final peptide product and does not require the amidation step.

Except where otherwise stated, the preferred dosage of the calcitonin mimetics of the present disclosure is identical for both therapeutic and prophylactic purposes. Desired dosages are discussed in more detail, infra, and differ depending on mode of administration.

Except where otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, tablet, injection or the like) commonly used in the pharmaceutical industry for delivery of peptide active agents is appropriate for use herein, and the terms "excipient", "diluent", or "carrier" includes such non-active ingredients as are typically included, together with active ingredients in such dosage form in the industry. A preferred oral dosage form is discussed in more detail, infra, but is not to be considered the exclusive mode of administering the active agents of the present disclosure.

The calcitonin mimetics of the present disclosure can be administered to a patient to treat a number of diseases or disorders. As used herein, the term "patient" means any organism belonging to the kingdom Animalia. In an embodiment, the term "patient" refers to vertebrates, more preferably, mammals including humans.

Accordingly, the present disclosure provides a method of treatment of type I diabetes, Type II diabetes or metabolic syndrome, obesity, or of appetite suppression, or for mitigating insulin resistance, or for reducing an undesirably high fasting serum glucose level, or for reducing an undesirably high peak serum glucose level, or for reducing an undesirably high peak serum insulin level, or for reducing an undesirably large response to a glucose tolerance test, or for treating osteoporosis, or for treating osteoarthritis.

As used herein, the term "glycemic control" refers to the typical levels of blood sugar (glucose) in a person with diabetes mellitus. The percentage of hemoglobin which is glycosolated (measured as hemoglobin A1c) is used as a proxy measure of long-term glycemic control.

As used herein, the term "improved glycemic control" refers to the ability of a calcitonin mimetic of the present disclosure to reduce the percentage of hemoglobin which is glycosolated.

There are a number of art-recognized measures of normal range for body weight in view of a number of factors such as gender, age and height. A patient in need of treatment or prevention regimens set forth herein include patients whose body weight exceeds recognized norms or who, due to heredity, environmental factors or other recognized risk factor, are at higher risk than the general population of becoming overweight or obese. In accordance with the present disclosure, it is contemplated that the calcitonin mimetics may be used to treat diabetes where weight control is an aspect of the treatment.

In an embodiment, the method includes enteral administration to a patient in need thereof for treatment of a said condition of a pharmaceutically effective amount of any one of the peptides described herein.

In an embodiment, the method includes parenteral administration to a patient in need thereof for treatment of a said condition of a pharmaceutically effective amount of any one of the peptides described herein. For parenteral administration (including intraperitoneal, subcutaneous, intravenous, intradermal or intramuscular injection), solutions of a peptide of the present disclosure in either sesame or peanut oil or in aqueous propylene glycol may be employed, for example. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Peptides may be formulated in sterile form in multiple or single dose formats such as being dispersed in a fluid carrier such as sterile physiological saline or 5% saline dextrose solutions commonly used with injectables.

Said method may include a preliminary step of determining whether the patient suffers from a said condition, and/or a subsequent step of determining to what extent said treatment is effective in mitigating the condition in said patient, e.g. in each case, carrying out an oral glucose tolerance test or a resting blood sugar level.

For improved control over the weight of the patient, to produce a loss of weight or an avoidance of weight gain, the active compound is preferably administered at least twice per day, e.g. from 2-4 times per day. Formulations of the active compound may contain a unit dosage appropriate for such an administration schedule. The active compounds may be administered with a view to controlling the weight of a patient undergoing treatment for diabetes or metabolic syndrome.

Oral enteral formulations are for ingestion by swallowing for subsequent release in the intestine below the stomach, and hence delivery via the portal vein to the liver, as opposed to formulations to be held in the mouth to allow transfer to the bloodstream via the sublingual or buccal routes.

Suitable dosage forms for use in the present disclosure include tablets, mini-tablets, capsules, granules, pellets, powders, effervescent solids and chewable solid formulations. Such formulations may include gelatin which is preferably hydrolysed gelatin or low molecular weight gelatin. Such formulations may be obtainable by freeze drying a homogeneous aqueous solution comprising calcitonin or a fragment or conjugate thereof and hydrolysed gelatin or low molecular weight gelatin and further processing the resulting solid material into said oral pharmaceutical formulation, and wherein the gelatin may have a mean molecular weight from 1000 to 15000 Daltons. Such formulations may include a protective carrier compound such as 5-CNAC or others as disclosed herein.

Whilst oral formulations such as tablets and capsules are preferred, compositions for use in the present disclosure may take the form of syrups, elixirs or the like and suppositories or the like. Oral delivery is generally the delivery route of choice since it is convenient, relatively easy and generally painless, resulting in greater patient compliance relative to other modes of delivery. However, biological, chemical and physical barriers such as varying pH in the gastrointestinal tract, powerful digestive enzymes, and active agent impermeable gastrointestinal membranes, makes oral delivery of calcitonin like peptides to mammals problematic, e.g. the oral delivery of calcitonins, which are long-chain polypeptide hormones secreted by the parafollicular cells of the thyroid gland in mammals and by the ultimobranchial gland of birds and fish, originally proved difficult due, at least in part, to the insufficient stability of calcitonin in the gastrointestinal tract as well as the inability of calcitonin to be readily transported through the intestinal walls into the blood stream.

Suitable oral formulations are however described below.

Treatment of Patients

In an embodiment, a calcitonin mimetic of the present disclosure is administered at adequate dosage to maintain serum levels of the mimetic in patients between 5 and 500 picograms per milliliter, preferably between 10 and 250 picograms per milliliter. The serum levels may be measured by radioimmunoassay techniques known in the art. The attending physician may monitor patient response, and may then alter the dosage somewhat to account for individual patient metabolism and response. Near simultaneous release is best achieved by administering all components of the present disclosure as a single pill or capsule. However, the disclosure also includes, for example, dividing the required amount of the calcitonin mimetic among two or more tablets or capsules which may be administered together such that they together provide the necessary amount of all ingredients. "Pharmaceutical composition," as used herein includes but is not limited to a complete dosage appropriate to a particular administration to a patient regardless of whether one or more tablets or capsules (or other dosage forms) are recommended at a given administration.

A calcitonin mimetic of the present disclosure may be formulated for oral administration using the methods employed in the Unigene Enteripep® products. These may include the methods as described in U.S. Pat. No. 5,912,014, U.S. Pat. No. 6,086,918, U.S. Pat. No. 6,673,574, U.S. Pat. No. 7,316,819, U.S. Pat. No. 8,093,207, and US Publication No. 2009/0317462. In particular, it may include the use of conjugation of the compound to a membrane translocator such as the protein transduction domain of the HIV TAT protein, co-formulation with one or more protease inhibitors, and/or a pH lowering agent which may be coated and/or an acid resistant protective vehicle and/or an absorption enhancer which may be a surfactant.

In an embodiment, a calcitonin mimetic of the present disclosure is preferably formulated for oral delivery in a manner known in U.S. Patent Publication No. 2009/0317462. One preferred oral dosage form in accordance with the present disclosure is set forth in Table 2 below:

TABLE 2

| ACTIVE AGENT OR EXCIPIENT | FUNCTION |
|---|---|
| A Calcitonin Mimetic selected from one of SEQ ID NO: 11 SEQ ID NO: 18 | Active agent |
| Coated Citric Acid Particles | Protease Inhibitor |
| Lauroylcarnitine | Absorption Enhancer |
| Nonionic Polymer | Subcoat |
| Eudragit L30D-55 | Enteric Coat |

In an embodiment, a calcitonin mimetic of the present disclosure may be formulated for enteral, especially oral, administration by admixture with a suitable carrier compound. Suitable carrier compounds include those described in U.S. Pat. No. 5,773,647 and U.S. Pat. No. 5,866,536 and amongst these, 5-CNAC (N-(5-chlorosalicyloyl)-8-aminooctaprylic acid, commonly as its disodium salt) is particularly effective. Other preferred carriers or delivery agents are SNAD (sodium salt of 10-(2-Hydroxybenzamido)decanoic acid) and SNAC (sodium salt of N-(8-[2-hydroxybenzoyl] amino)caprylic acid). In an embodiment, a pharmaceutical composition of the present disclosure comprises a delivery effective amount of carrier such as 5-CNAC, i.e. an amount sufficient to deliver the compound for the desired effect. Generally, the carrier such as 5-CNAC is present in an amount of 2.5% to 99.4% by weight, more preferably 25% to 50% by weight of the total composition.

In addition, WO 00/059863 discloses the disodium salts of formula I

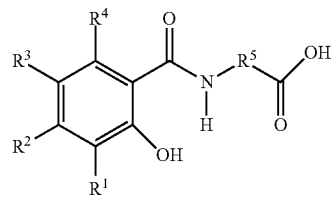

wherein $R^1$, $R^2$, $R^3$, and $R^4$ are independently hydrogen, —OH, —$NR^6R^7$, halogen, $C_1$-$C_4$ alkyl, or $C_1$-$C_4$ alkoxy; $R^5$ is a substituted or unsubstituted $C_2$-$C_{16}$ alkylene, substituted or unsubstituted $C_2$-$C_{16}$ alkenylene, substituted or unsubstituted $C_1$-$C_{12}$ alkyl(arylene), or substituted or unsubstituted aryl($C_1$-$C_{12}$ alkylene); and $R^6$ and $R^7$ are independently hydrogen, oxygen, or $C_1$-$C_4$ alkyl; and hydrates and solvates thereof as particularly efficacious for the oral delivery of active agents, such as calcitonins, e.g. salmon calcitonin, and these may be used in the present disclosure.

Preferred enteric formulations using optionally micronised 5-CNAC may be generally as described in WO2005/014031.

The compound may be formulated for oral administration using the methods employed in the Capsitonin product of Bone Medical Limited. These may include the methods incorporated in Axcess formulations. More particularly, the active ingredient may be encapsulated in an enteric capsule capable of withstanding transit through the stomach. This may contain the active compound together with a hydrophilic aromatic alcohol absorption enhancer, for instance as described in WO02/028436. In a known manner the enteric coating may become permeable in a pH sensitive manner, e.g. at a pH of from 3 to 7. WO2004/091584 also describes suitable formulation methods using aromatic alcohol absorption enhancers.

The compound may be formulated using the methods seen in the Oramed products, which may include formulation with omega-3 fatty acid as seen in WO2007/029238 or as described in U.S. Pat. No. 5,102,666.

Generally, the pharmaceutically acceptable salts (especially mono or di sodium salts), solvates (e.g. alcohol solvates) and hydrates of these carriers or delivery agents may be used.

Oral administration of the pharmaceutical compositions according to the disclosure can be accomplished regularly, e.g. once or more on a daily or weekly basis; intermittently, e.g. irregularly during a day or week; or cyclically, e.g. regularly for a period of days or weeks followed by a period without administration. The dosage form of the pharmaceutical compositions of the presently disclosed embodiments can be any known form, e.g. liquid or solid dosage forms. The liquid dosage forms include solution emulsions, suspensions, syrups and elixirs. In addition to the active compound and carrier such as 5-CNAC, the liquid formulations may also include inert excipients commonly used in the art such as, solubilizing agents e.g. ethanol; oils such as cottonseed, castor and sesame oils; wetting agents; emulsifying agents; suspending agents; sweeteners; flavourings; and solvents such as water. The solid dosage forms include capsules, soft-gel capsules, tablets, caplets, powders, granules or other solid oral dosage forms, all of which can be prepared by methods well known in the art. The pharmaceutical compositions may additionally comprise additives in amounts customarily employed including, but not limited to, a pH adjuster, a preservative, a flavorant, a taste-masking agent, a fragrance, a humectant, a tonicifier, a colorant, a surfactant, a plasticizer, a lubricant such as magnesium stearate, a flow aid, a compression aid, a solubilizer, an excipient, a diluent such as microcrystalline cellulose, e.g. Avicel PH 102 supplied by FMC corporation, or any combination thereof. Other additives may include phosphate buffer salts, citric acid, glycols, and other dispersing agents. The composition may also include one or more enzyme inhibitors, such as actinonin or epiactinonin and derivatives thereof; aprotinin, Trasylol and Bowman-Birk inhibitor.

Further, a transport inhibitor, i.e. a [rho]-glycoprotein such as Ketoprofin, may be present in the compositions of the present disclosure. The solid pharmaceutical compositions of the instant disclosure can be prepared by conventional methods e.g. by blending a mixture of the active compound, the carrier such as 5-CNAC, and any other ingredients, kneading, and filling into capsules or, instead of filling into capsules, molding followed by further tableting or compression-molding to give tablets. In addition, a solid dispersion may be formed by known methods followed by further processing to form a tablet or capsule. Preferably, the ingredients in the pharmaceutical compositions of the instant disclosure are homogeneously or uniformly mixed throughout the solid dosage form.

Alternatively, the active compound may be formulated as a conjugate with said carrier, which may be an oligomer as described in US2003/0069170, e.g.

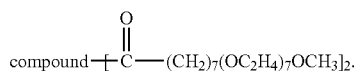

Such conjugates may be administered in combination with a fatty acid and a bile salt as described there.

Conujugates with polyethylene glycol (PEG) may be used, as described for instance in Mansoor et al.

Alternatively, active compounds may be admixed with nitroso-N-acetyl-D,L-penicillamine (SNAP) and Carbopol solution or with taurocholate and Carbapol solution to form a mucoadhesive emulsion.

The active compound may be formulated by loading into chitosan nanocapsules as disclosed in Prego et al. (optionally PEG modified as in Prego Prego C, Torres D, Fernandez-Megia E, Novoa-Carballal R, Quiñoá E, Alonso M J.) or chitosan or PEG coated lipid nanoparticles as disclosed in Garcia-Fuentes et al. Chitosan nanoparticles for this purpose may be iminothiolane modified as described in Guggi et al. They may be formulated in water/oil/water emulsions as described in Dogru et al. The bioavailability of active compounds may be increased by the use of taurodeoxycholate or lauroyl carnitine as described in Sinko et al. or in Song et al. Generally, suitable nanoparticles as carriers are discussed in de la Fuente et al and may be used in the present disclosure.

Other suitable strategies for oral formulation include the use of a transient permeability enhancer (TPE) system as described in WO2005/094785 of Chiasma Ltd. TPE makes use of an oily suspension of solid hydrophilic particles in a hydrophobic medium to protect the drug molecule from inactivation by the hostile gastrointestinal (GI) environment and at the same time acts on the GI wall to induce permeation of its cargo drug molecules.

Further included is the use of glutathione or compounds containing numerous thiol groups as described in US2008/0200563 to inhibit the action of efflux pumps on the mucous membrane. Practical examples of such techniques are described also in Caliceti, P. Salmaso, S., Walker, G. and Bernkop-Schnurch, A. (2004) 'Development and in vivo evaluation of an oral insulin-PEG delivery system.' Eur. J. Pharm. Sci., 22, 315-323, in Guggi, D., Krauland, A. H., and Bernkop-Schnurch, A. (2003) 'Systemic peptide delivery via the stomach: in vivo evaluation of an oral dosage form for salmon calcitonin'. J. Control. Rel. 92, 125-135, and in Bernkop-Schnurch, A., Pinter, Y., Guggi, D., Kahlbacher, H., Schöffmann, G., Schuh, M., Schmerold, I., Del Curto, M. D., D'Antonio, M., Esposito, P. and Huck, Ch. (2005) 'The use of thiolated polymers as carrier matrix in oral peptide delivery'—Proof of concept. J. Control. Release, 106, 26-33.

The active compound may be formulated in seamless micro-spheres as described in WO2004/084870 where the active pharmaceutical ingredient is solubilised as an emulsion, microemulsion or suspension, formulated into minispheres; and variably coated either by conventional or novel coating technologies. The result is an encapsulated drug in "pre-solubilised" form which when administered orally provides for predetermined instant or sustained release of the active drug to specific locations and at specific rates along the gastrointestinal tract. In essence, pre-solubilization of the drug enhances the predictability of its kinetic profile while simultaneously enhancing permeability and drug stability.

One may employ chitosan coated nanocapsules as described in US2009/0074824. The active molecule administered with this technology is protected inside the nanocapsules since they are stable against the action of the gastric fluid. In addition, the mucoadhesive properties of the system enhances the time of adhesion to the intestine walls (it has been verified that there is a delay in the gastrointestinal transit of these systems) facilitating a more effective absorption of the active molecule.

Methods developed by TSRI Inc. may be used. These include Hydrophilic Solubilization Technology (HST) in which gelatin, a naturally derived collagen extract carrying both positive and negative charges, coats the particles of the active ingredient contained in lecithin micelles and prevents their aggregation or clumping. This results in an improved wettability of hydrophobic drug particles through polar interactions. In addition, the amphiphilic lecithin reduces surface tension between the dissolution fluid and the particle surface.

The active ingredient may be formulated with cucurbiturils as excipients.

Alternatively, one may employ the GIPET technology of Merrion Pharmaceuticals to produce enteric coated tablets containing the active ingredient with an absorption enhancer which may be a medium chain fatty acid or a medium chain fatty acid derivative as described in US2007/0238707 or a membrane translocating peptide as described in U.S. Pat. No. 7,268,214.

One may employ GIRES™ technology which consists of a controlled-release dosage form inside an inflatable pouch, which is placed in a drug capsule for oral administration. Upon dissolution of the capsule, a gas-generating system inflates the pouch in the stomach. In clinical trials the pouch has been shown to be retained in the stomach for 16-24 hours.

Alternatively, the active may be conjugated to a protective modifier that allows it to withstand enzymatic degradation in the stomach and facilitate its absorption. The active may be conjugated covalently with a monodisperse, short-chain methoxy polyethylene glycol glycolipids derivative that is crystallized and lyophilized into the dry active pharmaceutical ingredient after purification. Such methods are described in U.S. Pat. No. 5,438,040.

One may also employ a hepatic-directed vesicle (HDV) for active delivery. An HDV may consist of liposomes (≤150 nm diameter) encapsulating the active, which also contain a hepatocyte-targeting molecule in their lipid bilayer. The targeting molecule directs the delivery of the encapsulated active to the liver cells and therefore relatively minute amounts of active are required for effect. Such technology is described in US2009/0087479.

The active may be incorporated into a composition containing additionally a substantially non-aqueous hydrophilic medium comprising an alcohol and a cosolvent, in association with a medium chain partial glyceride, optionally in admixture with a long-chain PEG species as described in US2002/0115592 in relation to insulin.

Alternatively, use may be made of intestinal patches as described in Shen Z, Mitragotri S, Pharm Res. 2002 April; 19(4):391-5 'Intestinal patches for oral drug delivery'.

The active may be incorporated into an erodible matrix formed from a hydrogel blended with a hydrophobic polymer as described in U.S. Pat. No. 7,189,414.

Suitable oral dosage levels for adult humans to be treated may be in the range of 0.05 to 5 mg, preferably about 0.1 to 2.5 mg.

The frequency of dosage treatment of patients may be from 1 to six times daily, for instance from two to four times daily. Treatment will desirably be maintained over a prolonged period of at least 6 weeks, preferably at least 6 months, preferably at least a year, and optionally for life.

Combination treatments for relevant conditions may be carried out using a composition according to the present disclosure and separate administration of one or more other therapeutics. Alternatively, the composition according to the present disclosure may incorporate one or more other therapeutics for combined administration.

Combination therapies according to the present disclosure include combinations of an active compound as described with insulin, GLP-2, GLP-1, GIP, or amylin, or generally with other anti-diabetics. Thus combination therapies including co-formulations may be made with insulin sensitizers including biguanides such as Metformin, Buformin and Phenformin, TZD's (PPAR) such as Balaglitazone, Pioglitazone, Rivoglitazone, Rosiglitazone and Troglitazone, dual PPAR agonists such as Aleglitazar, Muraglitazar and Tesaglitazar, or secretagogues including sulphonylureas such as Carbutamide, Chloropropamide, Gliclazide, Tolbutamide, Tolazamide, Glipizide, Glibenclamide, Glyburide, Gliquidone, Glyclopyramide and Glimepriride, Meglitinides/glinides (K+) such as Nateglinide, Repaglinide and Mitiglinide, GLP-1 analogs such as Exenatide, Liraglutide and Albiglutide, DPP-4 inhibitors such as Alogliptin, Linagliptin, Saxagliptin, Sitagliptin and Vildagliptin, insulin analogs or special formulations such as (fast acting) Insulin lispro, Insulin aspart, Insulin glulisine, (long acting) Insulin glargine, Insulin detemir), inhalable insulin—Exubra and NPH insulin, and others including alpha-glucosidase inhibitors such as Acarbose, Miglitol and Voglibose, amylin analogues such as Pramlintide, SGLT2 inhibitors such as Dapagliflozin, Remogliflozin and Sergliflozin as well as miscellaneous ones including Benfluorex and Tolrestat.

Further combinations include co-administration or co-formulation with leptins. Leptin resistance is a well-established component of type 2 diabetes; however, injections of leptin have so far failed to improve upon this condition. In contrast, there is evidence supporting that amylin, and thereby molecules with amylin-like abilities, as the salmon calcitonin mimetics, are able to improve leptin sensitivity. Amylin/leptin combination has shown a synergistic effect on body weight and food intake, and also insulin resistance [Kusakabe T et al]. Accordingly, the present disclosure provides a compound of the formula Ac-CSNLSTCVLG KLSQELHKLQ TYPRTDVGAN AP-NH$_2$ (SEQ ID NO: 15), which will be referred to herein as 'calcitonin mimetic 1' or 'UGP302'.

Accordingly, the present disclosure includes a pharmaceutical formulation of such a peptide for enteral administration, e.g. for treating type I diabetes, type II diabetes, or metabolic syndrome, or for mitigating insulin resistance, or for reducing an undesirably high fasting serum glucose level, or for reducing an undesirably high peak serum glucose level, or for reducing an undesirably high peak serum insulin level, or for reducing an undesirably high response to a glucose tolerance test, or for treating osteoporosis, or for treating osteoarthritis. The formulation may comprise also a carrier serving to enable effective enteral administration of said active compound.

Preferably, said formulation is formulated for oral administration to the digestive tract.

Preferably, said carrier comprises 5-CNAC, SNAD, or SNAC.

Additionally, the present disclosure includes said peptides as new compounds.

The presently disclosed embodiments is described in the following Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the described embodiments, and are not intended to limit the scope of the present disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Chronic Effect of Calcitonin Mimetic 1 (CM1) Compared to sCT

Animals

The study was performed in male Levin-DIO rats (diet-sensitive) and Levin-DR (diet-resistant) (TacLevin: CD (SD) DDIO) (Taconic, Hudson, N.Y., U.S.A.) obtained at age 6-7 weeks. On arrival, DIO rats were given high fat diet (60 kcal %) (#D12495, Research Diets Inc., New Brunswick, N.J., USA) and kept on the same diet for 16 weeks prior to and during the experiment. DR rats were given low-fat diet and served as control group. Animals were pair-wise housed throughout the study. Rats were handled and pre-dosed once daily with MilliQ H$_2$O for 2-3 weeks prior to experimental start to reduce stress-induced hyperglycaemia. Baseline parameters were recorded in an fasting (6 h) condition. Rats were randomized into treatment groups based on fasting body weight (BW) and fasting plasma glucose (FPG). Body weight, food and water intake were recorded once weekly during the study period.

Compound

Oral sCT or calcitonin mimetic 1 solution was prepared on the day of dosing by mixing a carrier with the given compound based on the following calculations:

5-CNAC (Vehicle):

Animals treated with oral 5-CNAC received a dose of 150 mg/kg dissolved in milliQ H20.

Dosage-level for 5-CNAC: 150 mg/kg

Dosing volume: 5 ml/kg

Compound concentration: 30 mg/ml sCT/Calcitonin Mimetic 1:

Animals treated with oral sCT or oral calcitonin mimetic 1 received doses of 1.0 mg/kg combined with 150 mg/kg 5-CNAC—all dissolved in milliQ H20.
Dosage-level for sCT/calcitonin mimetic 1: 1.0 mg/kg
Dosing volume: 5 ml/kg
Compound concentration: 0.2 mg/ml Drug administration by per oral (p.o.) gavage b.i.d. (7-8 am and 3-4 pm) during the study period and as single dose in the morning prior to start of OGTT.

Oral gavage of glucose during OGTT was prepared by the following calculation:
D-Glucose:
Animals were given 2 g/kg single dose dissolved in milliQ H20.
Dosage-level for D-Glucose: 2 g/kg
Dosing volume: 4 ml/kg
Compound concentration: 500 mg/ml
Experimental Setup:

| Baseline | Week 1 | Week 2 | Week 3 | Week 4 |
|---|---|---|---|---|
| FPG | BW | BW | BW | BW |
| BW | Food | Food | Food | Food |
| B | | FPG | | FPG |
| | | B | | B |
| | | OGTT | | |

FPG = Fasting Plasma Glucose;
BW = Body Weight;
B = Blood;
OGTT = Oral Glucose Tolerance Test OGTT Following Overnight Fasting (16 h):

| −30 | 0 | 15 | 30 | 60 | 120 | 240 min |
|---|---|---|---|---|---|---|
| D | G | B | B | B | B | B |
| B | B | BG | BG | BG | BG | BG |
| BG | BG | | | | | |

D = Drug;
BG = Blood glucose;
B = Blood;
G = Glucose

Blood sampling and glycemia were measured by heated tail venous puncture.

Whole blood glucose levels were determined with an ACCU-CHEK® Avia blood glucose meter (Roche Diagnostics, Rotkreuz, Switzerland). Blood (approx 300 ul) is collected in 1 ml MiniCollect K3EDTA plasma-tube (Greiner-Bio-One GmbH, Frickenhausen, Germany), inverted, and stored on ice. Tubes are centrifuged 3000×g (5000 rpm in table centrifuge) for 10 min at 4° C. and plasma obtained. Plasma samples are stored at −20° C. until analysis. A total of ~2.5 ml blood is obtained during OGTT (~0.3% of body weight).

Experimental Groups

| Intervention | Compound | Conc. | Number |
|---|---|---|---|
| Oral vehicle | 5-CNAC | 150 mg/kg | n = 10 |
| Oral sCT | 5-CNAC + sCT | 150 mg/kg + 1 mg/kg | n = 10 |
| Oral calcitonin mimetic 1 | 5-CNAC + calcitonin mimetic 1 | 150 mg/kg + 1 mg/kg | n = 10 |

Statistics

Statistical analysis was performed by one-way ANOVA followed by the Dunnett's post hoc test for multiple comparison. Student's t-test was performed to compare two paired group. All analysis was performed using GRAPHPAD PRISM software (GraphPad Prism, San Diego, Calif. U.S.A). Incremental area under curve (iAUC) during OGTT was calculated by the trapezoidal method. A value of P<0.05 was considered to be significant. All data are presented as mean±standard error of the mean (SEM).

Figure 1B:
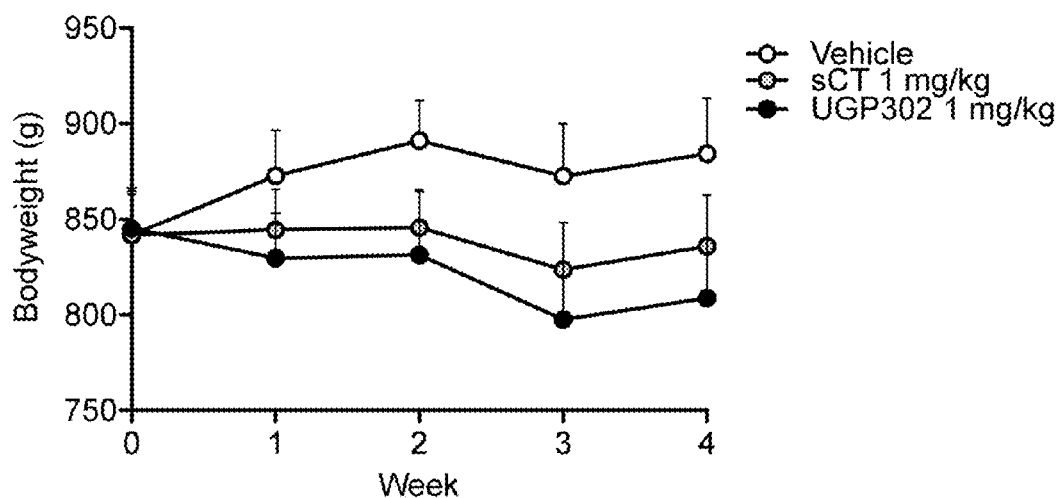
Figure 1C:
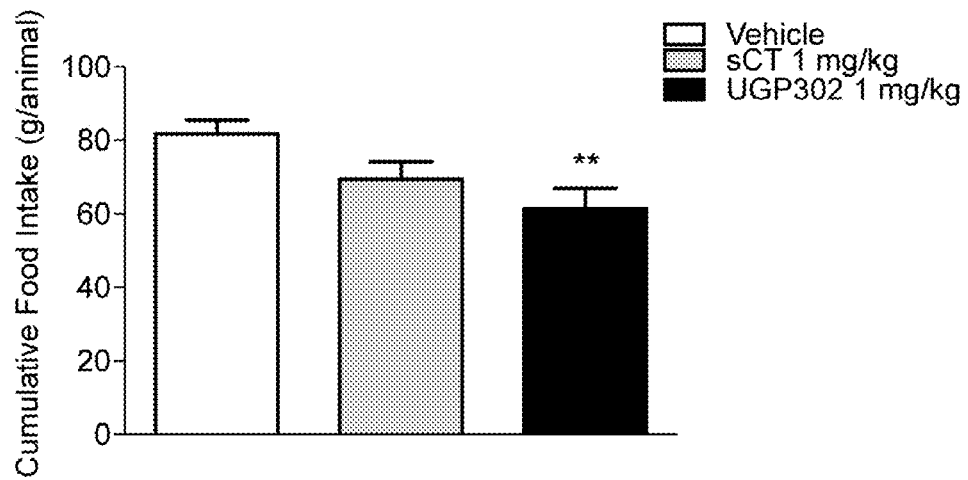
Figure 1D:
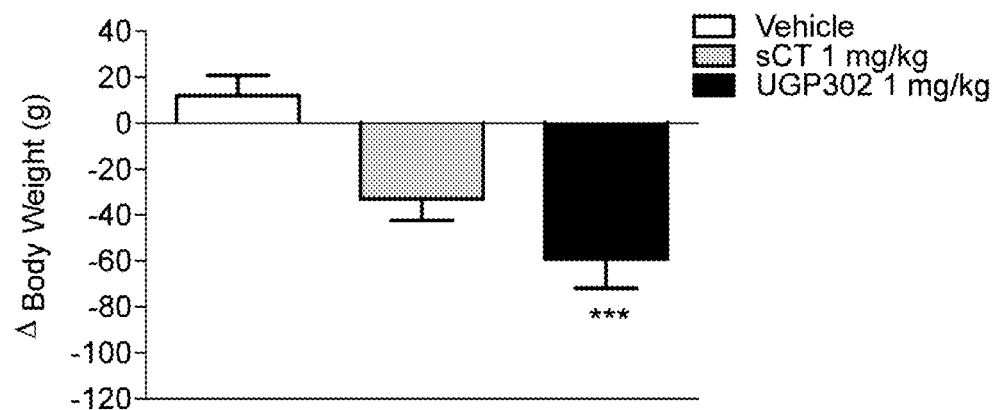
Figure 2A:
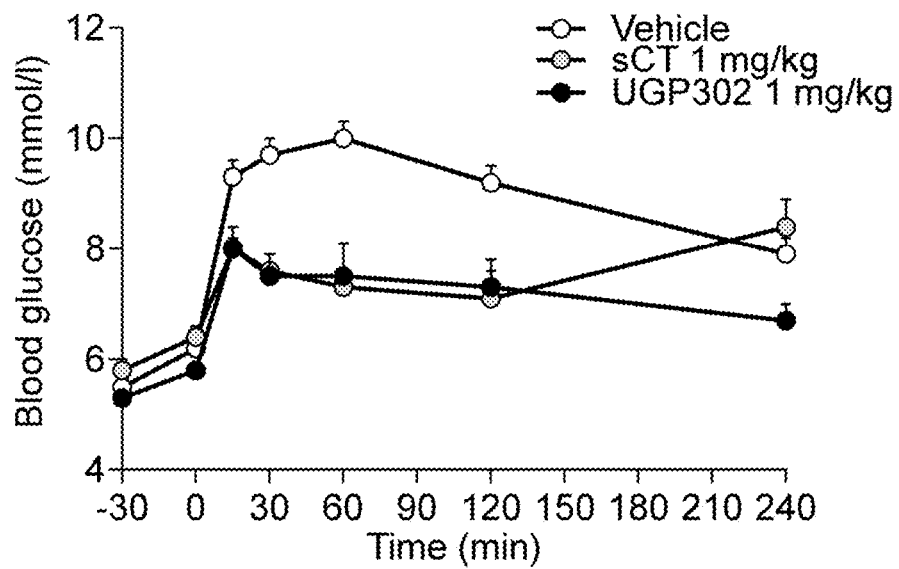
FIG. 2A and FIG. 2B show the effect of oral sCT versus oral UGP 302 on glucose tolerance during OGTT in DIO rats as measured in Example 1.
Figure 2B:
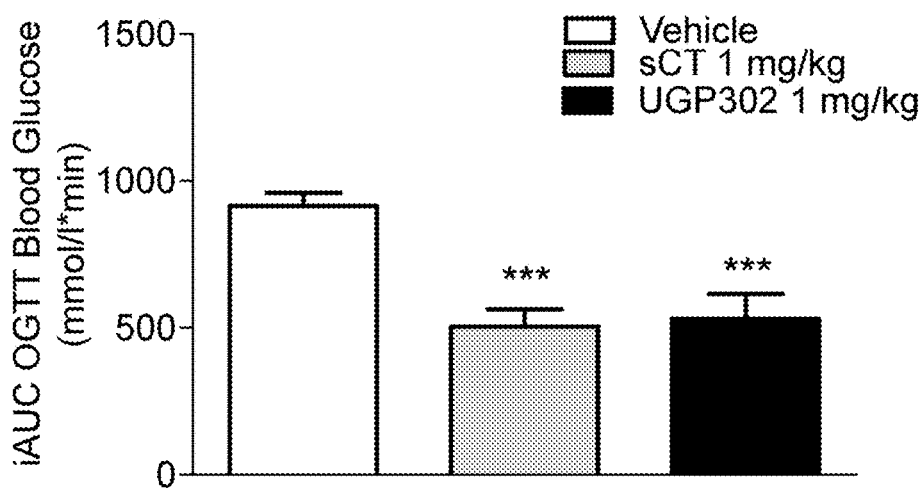
Figure 3:
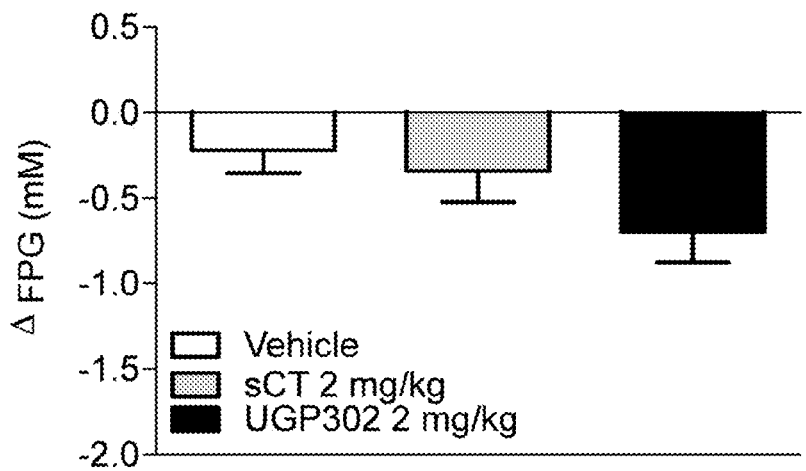
FIG. 3 shows the effect of oral sCT versus oral UGP 302 on fasting glycemia in DIO rats as measured in Example 1.

Results
Baseline Characteristics:

Results are summarized in FIGS. 1A-1D (Food intake and body weight), FIGS. 2A-2B (OGTT) and FIG. 3 (FPG). FIG. 1A, FIG. 1B, FIG. 1C, and FIG. 1D show the effect of chronic oral salmon calcitonin ("sCT") versus oral UGP 302 administration on body weight and food intake in DIO rats as measured in Example 1. FIG. 2A and FIG. 2B show the effect of oral sCT versus oral UGP 302 on glucose tolerance during OGTT in DIO rats as measured in Example 1. FIG. 3 shows the effect of oral sCT versus oral UGP 302 on fasting glycemia in DIO rats as measured in Example 1;

One dose of oral sCT/calcitonin mimetic 1 containing 1 mg/kg compound was applied by gavage twice daily to four groups of rats for 4 weeks. An oral vehicle group served as dosing regimen control, respectively. * P<0.05,  P<0.01, * P<0.001 vs Vehicle. Results are presented as means±SEM.

The 16-weeks ad libitum high-fat diet induced a pronounced obese phenotype in the diet-sensitive (DIO) rats when comparing body weight to their diet-resistant (DR) littermates (P<0.001) (Table 3). 6-hrs Fasting glycemia was not different between DIO and DR. In contrast, area under curve (AUC) calculations during OGTT was significantly higher in DIO rats compared to DR rats, demonstrating the high-fat diet-induced glucose intolerance (Table 3).

TABLE 3

Metabolic parameters in DIO and DR rats

| | Diet-resistant (DR) | Diet-sensitive (DIO) |
|---|---|---|
| Body Weight (g) | 609.5 ± 24.5 | 841.8 ± 22.9*** |
| Fasting plasma glucose (mM) | 6.5 ± 0.1 | 6.8 ± 0.2 |
| AUC in OGTT Blood glucose (mM*min) | 625.1 ± 20.5 | 914.3 ± 44.6*** |

AUC, area under curve; OGTT, oral glucose tolerance test.
Data are means ± SEM (n = 12/DR) n = 24/DIO).

Body Weight and Food Intake

During the first week of treatment administration of oral sCT significantly reduced food intake compared to oral vehicle treated rats. Furthermore, oral sCT protected against further gain in body weight as observed for oral vehicle group (FIGS. 1A-1D). Thus, these observations confirm the acute strong anorectic action induced by application of oral sCT in DIO rats. Interestingly, from week 2 of treatment and throughout the study period, food intake normalized in oral sCT treated rats and resembled ingestion by oral vehicle resulting in a lack of difference in regards to cumulative food intake at study end. This confirms previously reports suggesting a transient effect of oral sCT upon energy intake. However, throughout the study period, oral sCT sustained the protecting effect on body weight gain and significantly reduced body weight from baseline when compared to oral vehicle at study end (FIGS. 1A-1B). This is in line with a possibly endogenous effect of oral sCT upon energy expenditure to chronically regulate energy balance.

Generally, oral application of calcitonin mimetic 1 resembled the strong anorectic action of oral sCT during the initial week of treatment and significantly reduced food intake and protected against gain in body weight compared to oral vehicle group (FIG. 1). As observed for oral sCT, calcitonin mimetic 1 exerted a transient effect on food intake, although food intake trended reduced when compared to oral sCT during the study period. Thus, following four weeks of treatment cumulative food intake was significantly reduced in calcitonin mimetic 1 when compared to oral vehicle. Furthermore, when compared to oral sCT, a more pronounced significant reduction in body weight was observed suggesting superiority in regards to effect on energy balance.

Glucose Tolerance:

Results are shown in FIGS. 2A-2B. One dose of oral sCT/calcitonin mimetic 1 containing 1 mg/kg compound were applied by gavage twice daily to four groups of rats for 4 weeks. An oral vehicle group served as dosing regimen control. OGTT performed following 2 weeks of treatment after overnight-fasting.*** $P<0.001$ vs Vehicle. Results are presented as means±SEM.

Oral sCT significantly reduced glucose iAUC during OGTT after 2 weeks of treatment compared to oral vehicle, thus confirming the postprandial glycemic control exerted by oral application of sCT as previously demonstrated. In general, calcitonin mimetic 1 demonstrated a similar significant reduction in iAUC as observed for oral sCT, although with no clear superiority to oral sCT in this respect.

Fasting Glycaemia:

Following 2 and 4 weeks of treatment, oral sCT application was not significantly different from oral vehicle treated rats, which is in contrast with previously observations in male DIO rats, in where a 1-1.5 mM reduction in fasting blood glucose typically is observed following chronic treatment. For calcitonin mimetic 1, a trend towards superiority in fasting glycaemia was observed throughout the study period when compared to oral vehicle or oral sCT.

EXAMPLE 2

Acute and Short Term Effects of Oral sCT Versus Oral Calcitonin Mimetic 1

Animals

The study was performed in male Levin-DIO rats (diet-sensitive) and Levin-DR (diet-resistant) (TacLevin: CD (SD) D10) (Taconic, Hudson, N.Y., U.S.A.) obtained at age 6-7 weeks. On arrival, DIO rats were given high fat diet (60 kcal %) (#D12495, Research Diets Inc., New Brunswick, N.J., USA) and kept on the same diet for 12 weeks prior to and during the experiment. DR rats were given low-fat diet and served as control group. Animals were pair-wise housed throughout the study. Rats were handled and pre-dosed once daily with MilliQ $H_2O$ for 2-3 weeks prior to experimental start to reduce stress-induced hyperglycaemia. On the day prior to study start animals were given a single dose of vehicle. Baseline parameters were recorded in an overnight fasting (16 h) condition. Rats were randomized into treatment groups based on fasting body weight (BW) and fasting plasma glucose (FPG). Body weight, food and water intake were recorded prior to and at study end.

Compounds

Oral sCT/calcitonin mimetic 1 solution was prepared on the day of dosing by mixing the carrier with the given compound based on the following calculations:

5-CNAC (Vehicle):

Animals treated with oral 5-CNAC received a dose of 150 mg/kg dissolved in milliQ H20.

Dosage-level for 5-CNAC: 150 mg/kg
Dosing volume: 5 ml/kg
Compound concentration: 30 mg/ml sCT/Calcitonin Mimetic 1:

Animals treated with oral sCT or oral calcitonin mimetic 1 received doses of 0.5 mg/kg, 1.0 mg/kg or 2.0 mg/kg combined with 150 mg/kg 5-CNAC—all dissolved in milliQ H20.

Dosage-level for sCT/calcitonin mimetic 1: 0.5 mg/kg
Dosing volume: 5 ml/kg
Compound concentration: 0.1 mg/ml
Dosage-level for sCT/calcitonin mimetic 1: 1.0 mg/kg
Dosing volume: 5 ml/kg
Compound concentration: 0.2 mg/ml
Dosage-level for sCT/calcitonin mimetic 1: 2.0 mg/kg
Dosing volume: 5 ml/kg
Compound concentration: 0.4 mg/ml Drug administration were given by per oral (p.o.) gavage b.i.d. during the study period and as single dose in the morning prior to start of OGTT.

Oral gavage of glucose during OGTT was prepared by the following calculation:

D-Glucose:

Animals were given 2 g/kg single dose dissolved in milliQ H20.

Dosage-level for D-Glucose: 2 g/kg
Dosing volume: 4 ml/kg
Compound concentration: 500 mg/ml Experimental Setup Acute Testing—Treatment Period for 0.5 mg/kg, 1 mg/kg and 2 mg/kg:

| Day 0 | Day 1-2 | Day 3 | Day 4 | Day 5 | Day 6 | Day 7 |
|---|---|---|---|---|---|---|
| $1^{st}$ OGTT All vehicle | Rest No handling | Pre-dose All vehicle | Treatment (b.i.d) | Treatment (b.i.d) | Treatment (b.i.d) | $2^{nd}$ OGTT Single dose |

Following the initial ($1^{st}$) OGTT, animals are randomized into treatment groups based on FBG and BW. Animals will be pre-treated 3 days (b.i.d.) prior to $2^{nd}$ OGTT. Dosing will be performed in the morning (7-8 am) and afternoon (3-4 pm).

The study was performed in an x-over design with each animal being its own control.

OGTT Following Overnight Fasting (16 h):

| −30 | 0 | 15 | 30 | 60 | 120 | 240 min |
|---|---|---|---|---|---|---|
| D B BG | G B BG | B BG | B BG | B BG | B BG | B BG |

D = Drug;
BG = Blood glucose;
B = Blood;
G = Glucose

Blood sampling and glycemia were measured by heated tail venous puncture.

Whole blood glucose levels were determined with an ACCU-CHEK® Avia blood glucose meter (Roche Diagnostics, Rotkreuz, Switzerland). Blood (approx 300 ul) is collected in 1 ml MiniCollect K3EDTA plasma-tube (Greiner-Bio-One GmbH, Frickenhausen, Germany), inverted, and stored on ice. Tubes are centrifuged 3000×g (5000 rpm in table centrifuge) for 10 min at 4° C. and plasma obtained.

Plasma samples are stored at −20° C. until analysis. A total of ~2.5 ml blood is obtained during OGTT (~0.3% of body weight).

Experimental Groups

| Intervention | Compound | Conc. | Number |
|---|---|---|---|
| Oral vehicle | 5-CNAC | 150 mg/kg | (4 groups of n = 8) X-over design to 0.5 mg/kg |
| Oral sCT | 5-CNAC + sCT | 150 mg/kg + 0.5 mg/kg | n = 8 |
| Oral calcitonin mimetic 1 | 5-CNAC + calcitonin mimetic 1 | 150 mg/kg 0.5 mg/kg | n = 8 |
| Oral vehicle | 5-CNAC | 150 mg/kg | (4 groups of n = 8) X-over design to 1 mg/kg |
| Oral sCT | 5-CNAC + sCT | 150 mg/kg + 1 mg/kg | n = 8 |
| Oral calcitonin mimetic 1 | 5-CNAC + calcitonin mimetic 1 | 150 mg/kg 1 mg/kg | n = 8 |
| Oral vehicle | 5-CNAC | 150 mg/kg | (4 groups of n = 8) X-over design to 2 mg/kg |
| Oral sCT | 5-CNAC + sCT | 150 mg/kg + 2 mg/kg | n = 8 |
| Oral calcitonin mimetic 1 | 5-CNAC + calcitonin mimetic 1 | 150 mg/kg 2 mg/kg | n = 8 |

Statistics

Statistical analysis was performed by one-way ANOVA followed by the Dunnett's post hoc test for multiple comparison. Student's t-test was performed to compare two paired group. All analysis was performed using GRAPH-PAD PRISM software (GraphPad Prism, San Diego, Calif. U.S.A). Incremental area under curve (iAUC) during OGTT was calculated by the trapezoidal method. A value of $P<0.05$ was considered to be significant. All data are presented as mean±standard error of the mean (SEM).

Results

Baseline Characteristics

The 12-weeks ad libitum high-fat diet induced a pronounced obese phenotype in the diet-sensitive (D10) rats when comparing body weight to their diet-resistant (DR) littermates ($P<0.001$) (Table 1). Fasting glycemia was not different between DIO and DR. In contrast, area under curve (AUC) calculations during OGTT was significantly higher in DIO rats compared to DR rats, demonstrating the high-fat diet-induced glucose intolerance (Table 4).

TABLE 4

Metabolic parameters in DIO and DR rats

| | Diet-resistant (DR) | Diet-sensitive (DIO) |
|---|---|---|
| Body Weight (g) | 609.5 ± 24.5 | 813.6 ± 9.8*** |
| Fasting plasma glucose (mM) | 5.8 ± 0.1 | 5.8 ± 0.2 |
| AUC in OGTT Blood glucose (mM*min) | 648.8 ± 27.3 | 888.4 ± 64.3*** |

AUC, area under curve; OGTT, oral glucose tolerance test.
Data are means ± SEM (n = 12/DR, n = 24/DIO).

Body Weight and Food Intake

Three different doses of oral sCT/calcitonin mimetic 1 containing 0.5, 1 and 2 mg/kg compound were applied by gavage twice daily to 4 groups of rats for 3 days. * $P<0.05$, ** $P<0.01$ vs oral sCT.

Figure 4A:
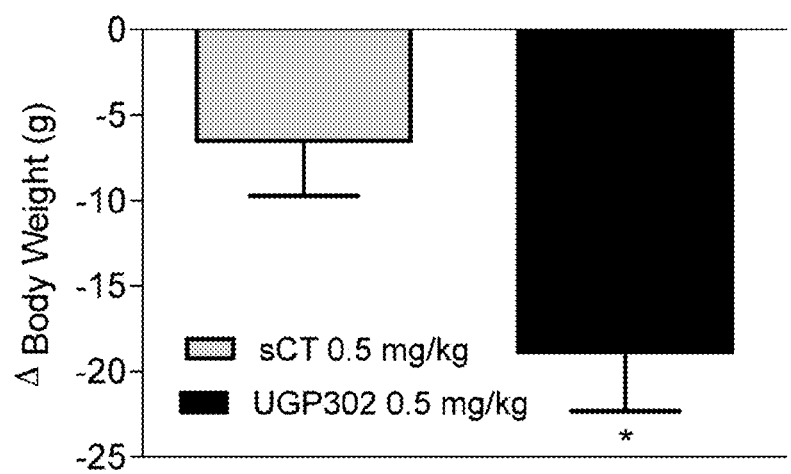
FIG. 4A and FIG. 4B show the effect of oral sCT versus oral UGP 302 on body weight (FIG. 4A) and food intake (FIG. 4B) in DIO rats observed in Example 2 at a first dosage.
Figure 4B:
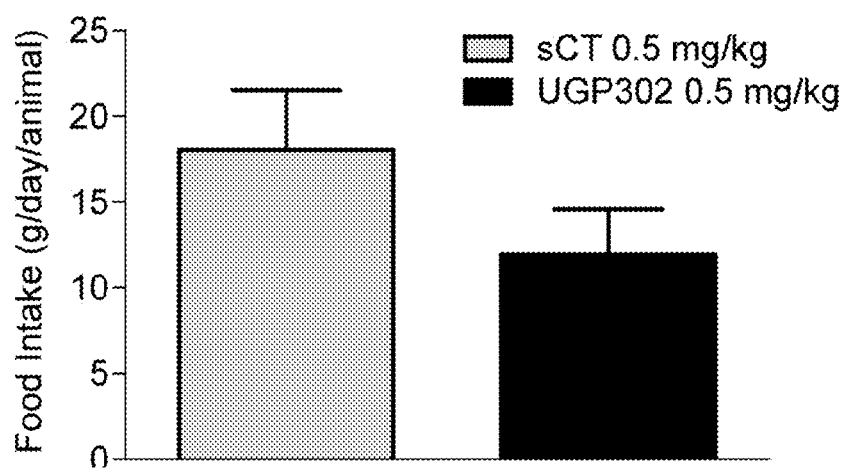
Figure 5A:
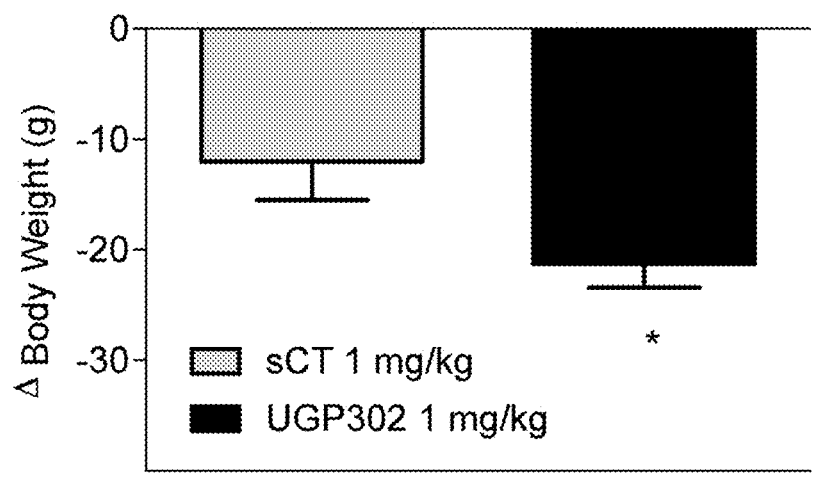
FIG. 5A and FIG. 5B show the effect of oral sCT versus oral UGP 302 on body weight (FIG. 5A) and food intake (FIG. 5B) in DIO rats observed in Example 2 at a second dosage.
Figure 5B:
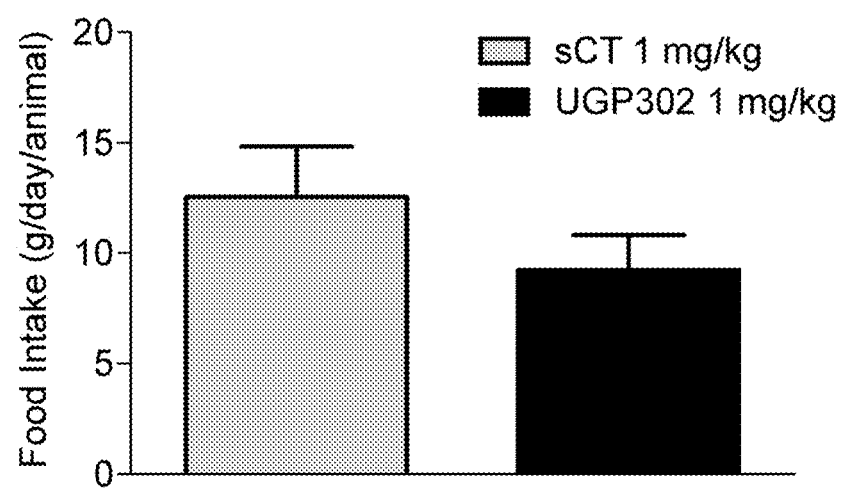
Figure 6A:
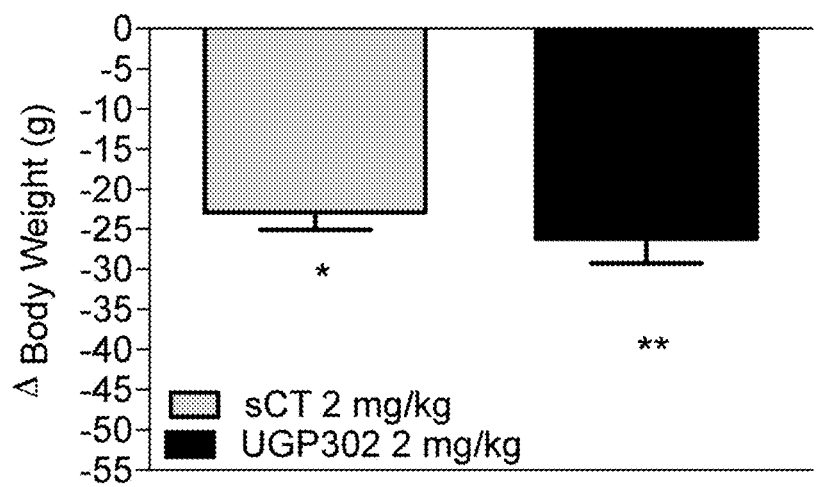
FIG. 6A and FIG. 6B show the effect of oral sCT versus oral UGP 302 on body weight (FIG. 6A) and food intake (FIG. 6B) in DIO rats observed in Example 2 at a third dosage.
Figure 6B:
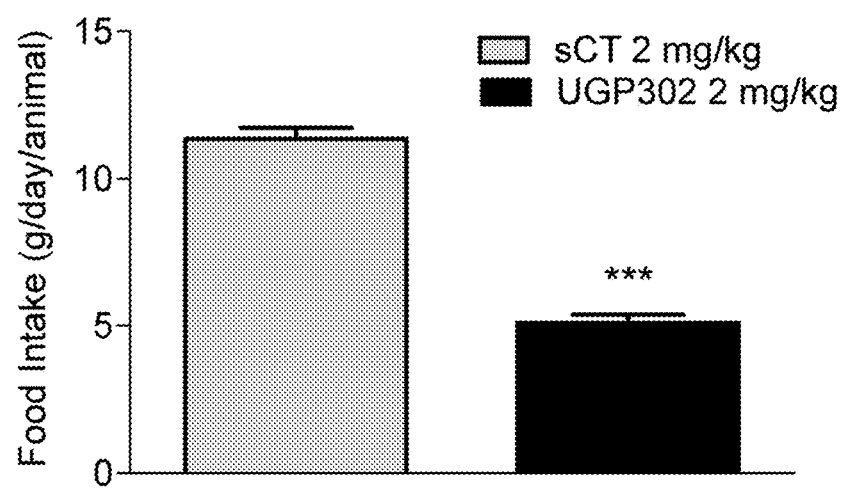

Results are presented in FIGS. 4A-4B, FIGS. 5A-5B, and FIGS. 6A-6B as means±SEM. FIG. 4A and FIG. 4B show the effect of oral sCT versus oral UGP 302 on body weight and food intake in DIO rats observed in Example 2 at a first dosage. FIG. 5A and FIG. 5B show the effect of oral sCT versus oral UGP 302 on body weight and food intake in DIO rats observed in Example 2 at a second dosage. FIG. 6A and FIG. 6B show the effect of oral sCT versus oral UGP 302 on body weight and food intake in DIO rats observed in Example 2 at a third dosage;

Oral sCT dose-dependently decreased body weight and food intake following the short-term treatment period and thus confirmed the anorectic action induced by targeting the amylin receptor as previously observed. In general, the mimetic demonstrated dose-dependent superiority to oral sCT in regards to reduction in body weight as illustrated in FIGS. 4A-4B, FIGS. 5A-5B and FIGS. 6A-6B. Application of calcitonin mimetic 1 at 0.5 mg/kg demonstrated significantly difference to oral sCT 0.5 mg/kg. The food intake for the mimetic trended dose-dependently reduced compared to oral sCT.

Glucose Tolerance

Figure 7A:
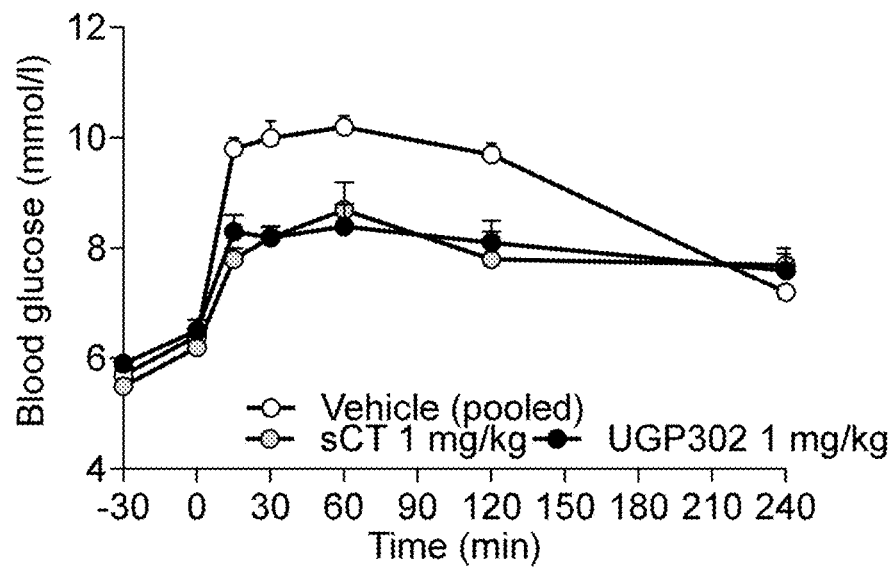
FIG. 7A and FIG. 7B show the effect of oral sCT versus oral UGP 302 at a first dosage on glucose tolerance during OGTT in DIO rats as measured in Example 2.
Figure 7B:
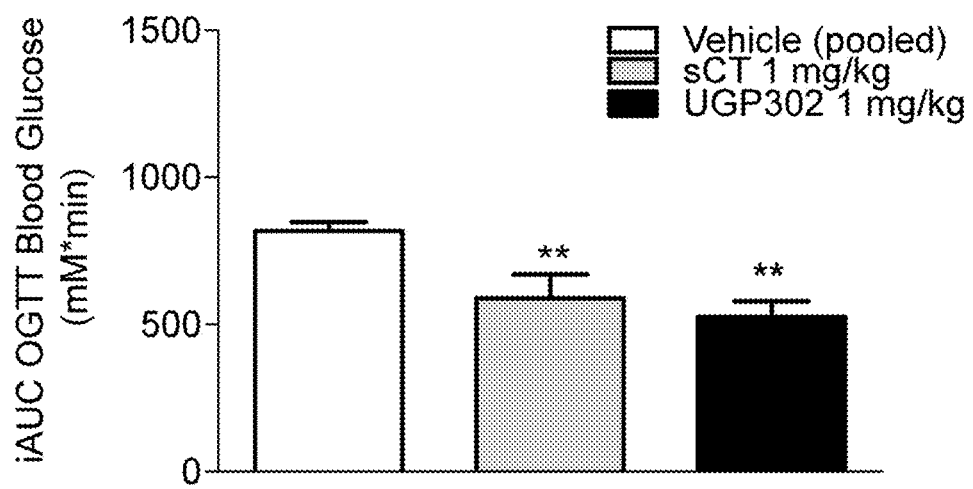
Figure 8A:
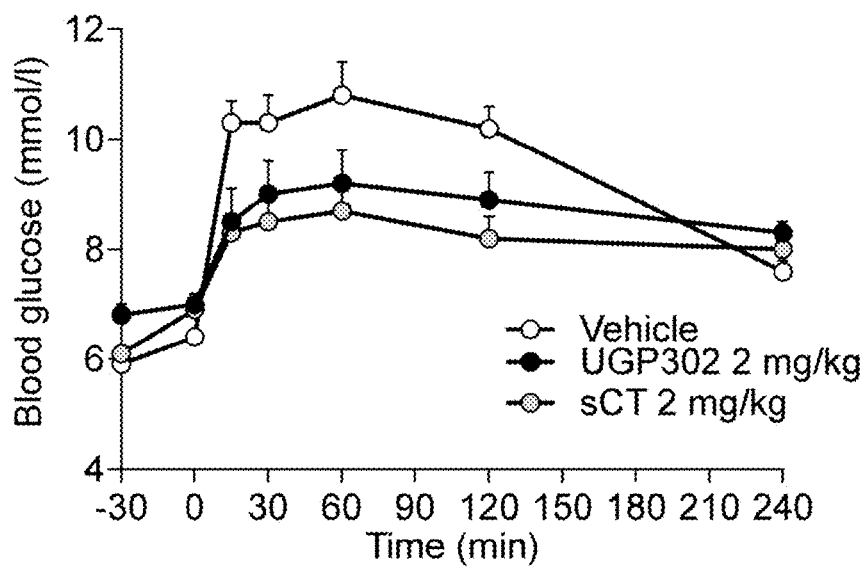
FIG. 8A and FIG. 8B show the effect of oral sCT versus oral UGP 302 at a second dosage on glucose tolerance during OGTT in DIO rats as measured in Example 2.
Figure 8B:
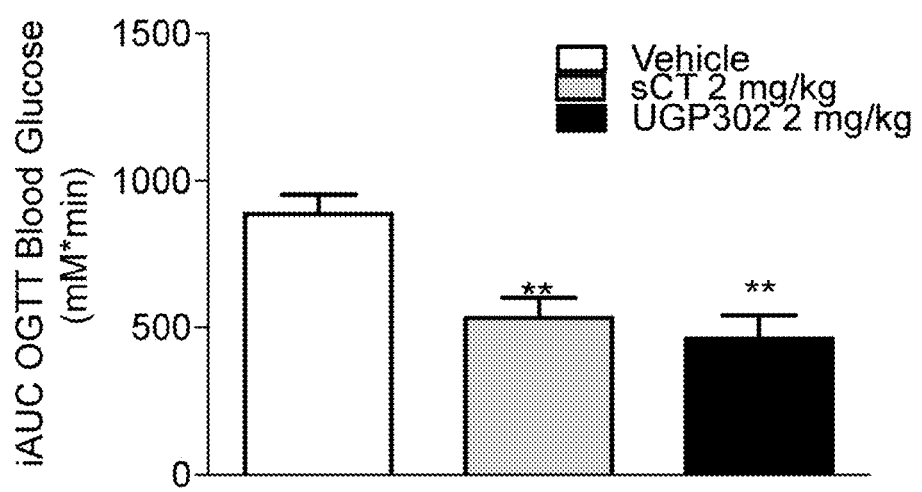
Figure 9A:
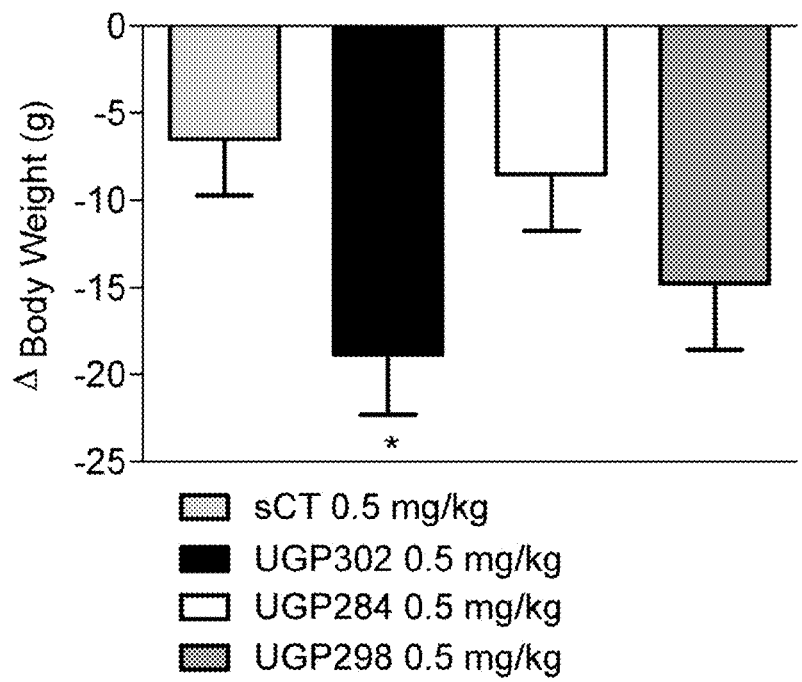
FIG. 9A, FIG. 9B, FIG. 9C, FIG. 9D, FIG. 9E, and FIG. 9F show the effect of oral sCT versus three oral UGPs on body weight (FIGS. 9A, 9C, 9E) and food intake (FIGS. 9B, 9C) in DIO rats as measured in Example 3.
Figure 9B:
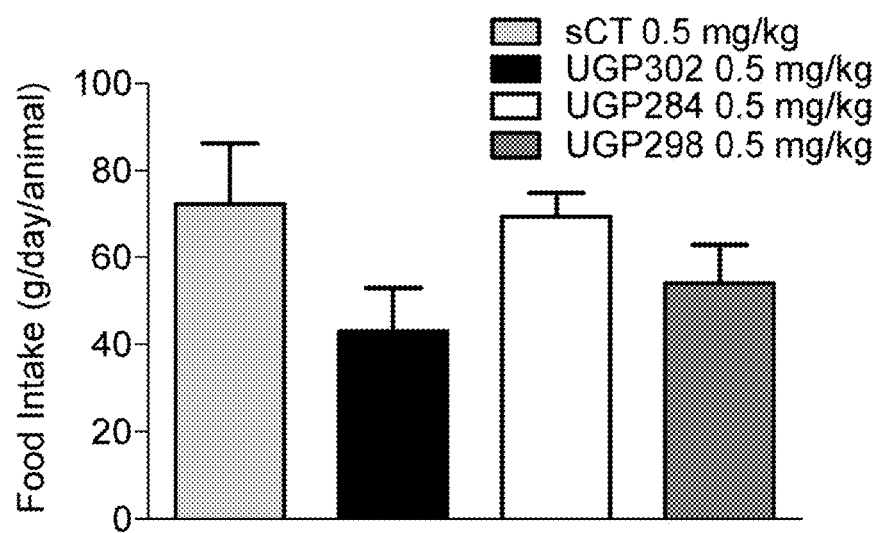
Figure 9C:
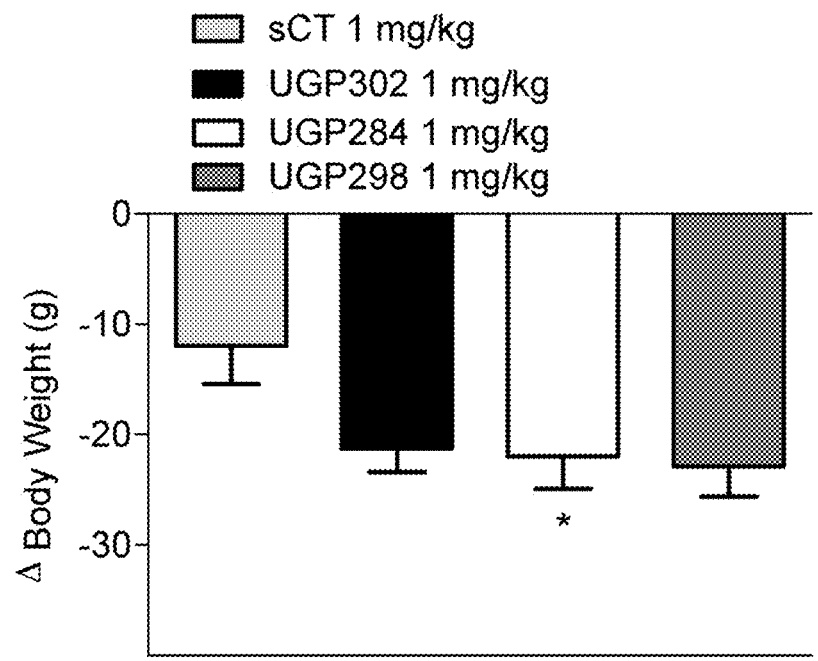
Figure 9D:
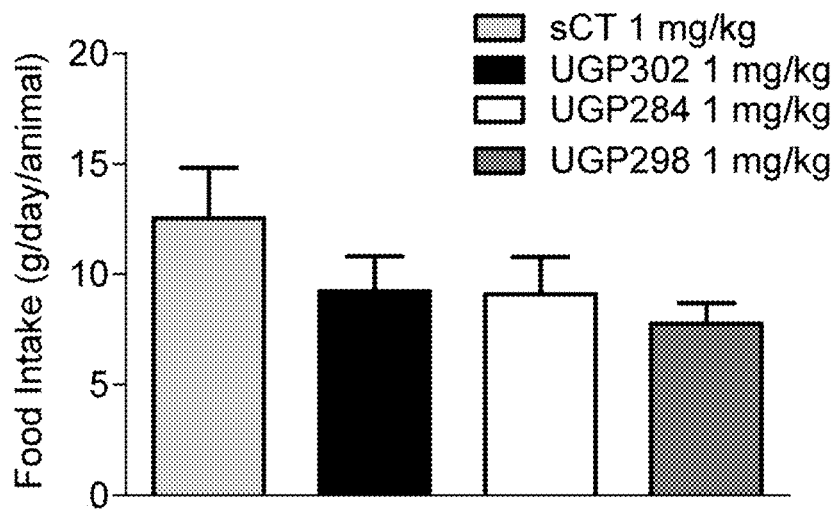
Figure 9E:
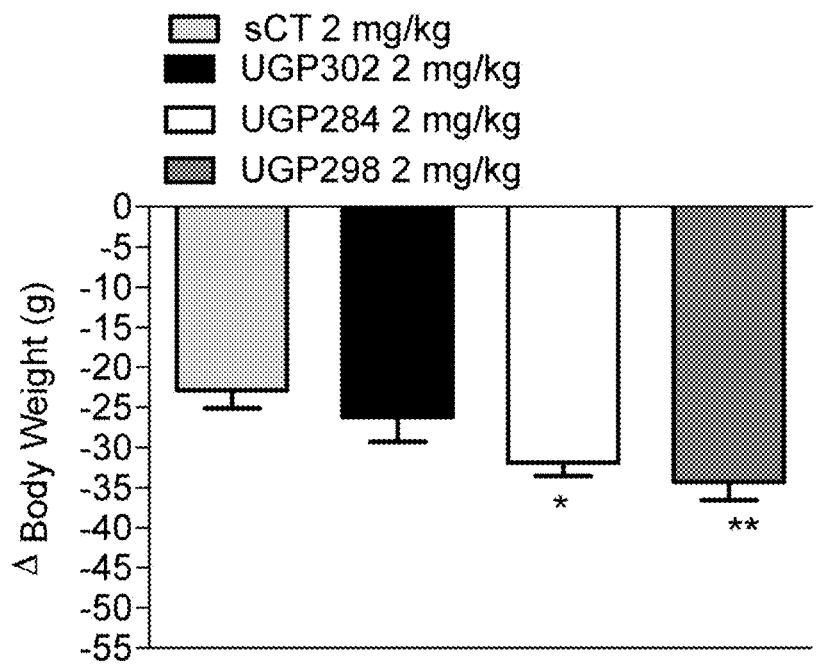
Figure 9F:
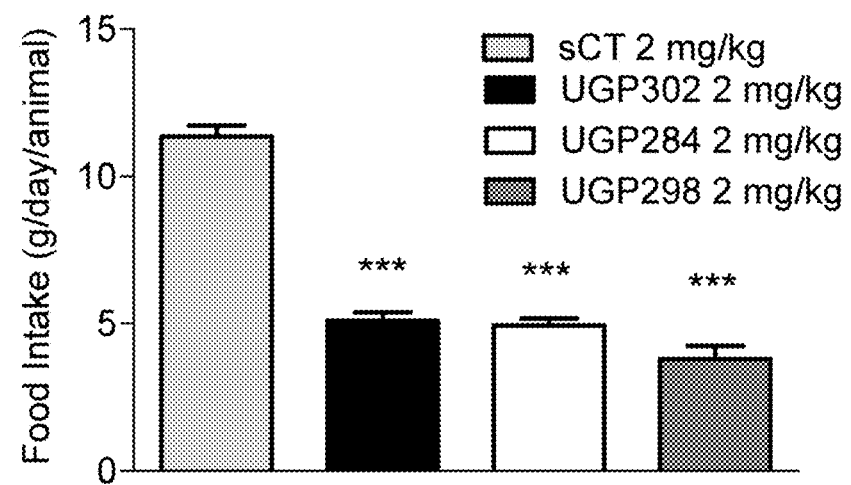
Figure 10A:
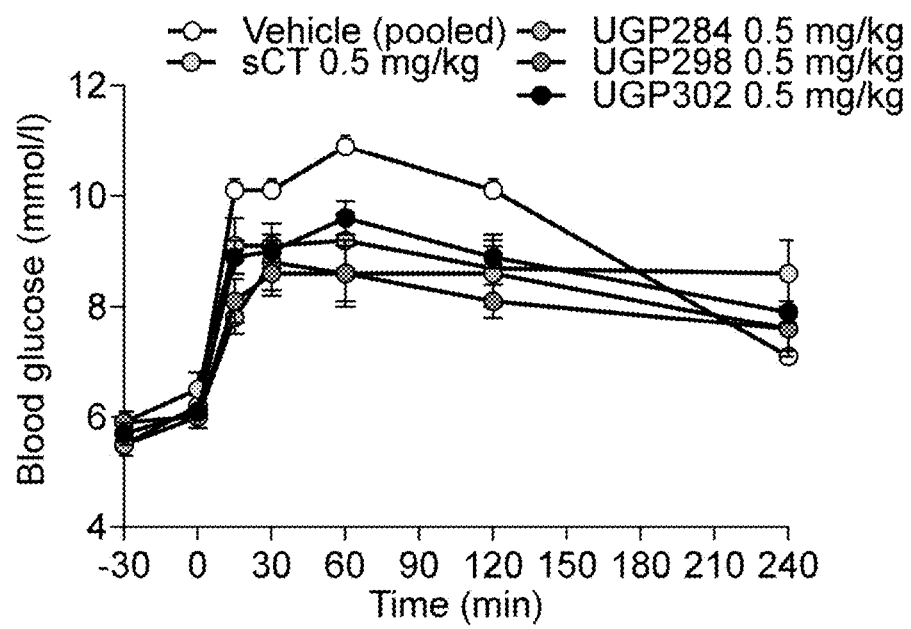
FIG. 10A, FIG. 10B, FIG. 10C, FIG. 10D, FIG. 10E, and FIG. 10F show the effect of oral sCT versus three oral UGPs on glucose levels in a glucose tolerance test in DIO rats as measured in Example 3.
Figure 10B:
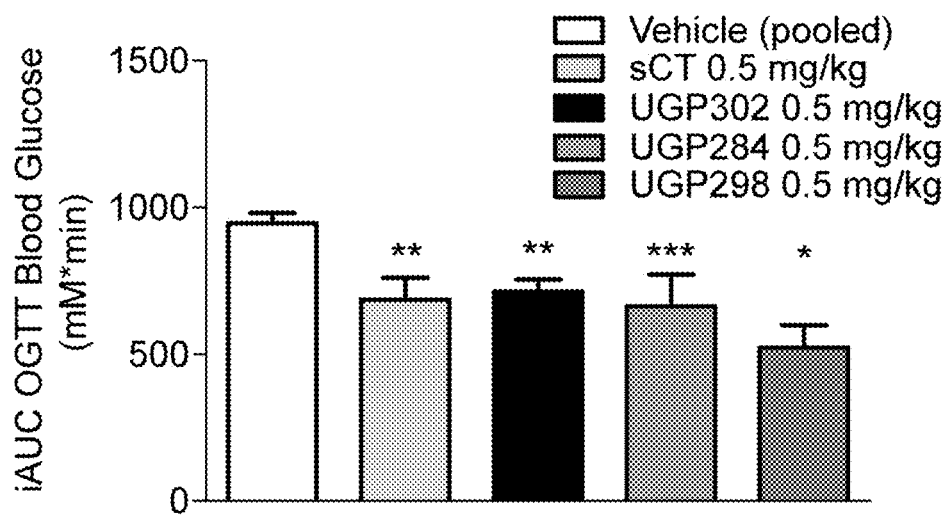
Figure 10C:
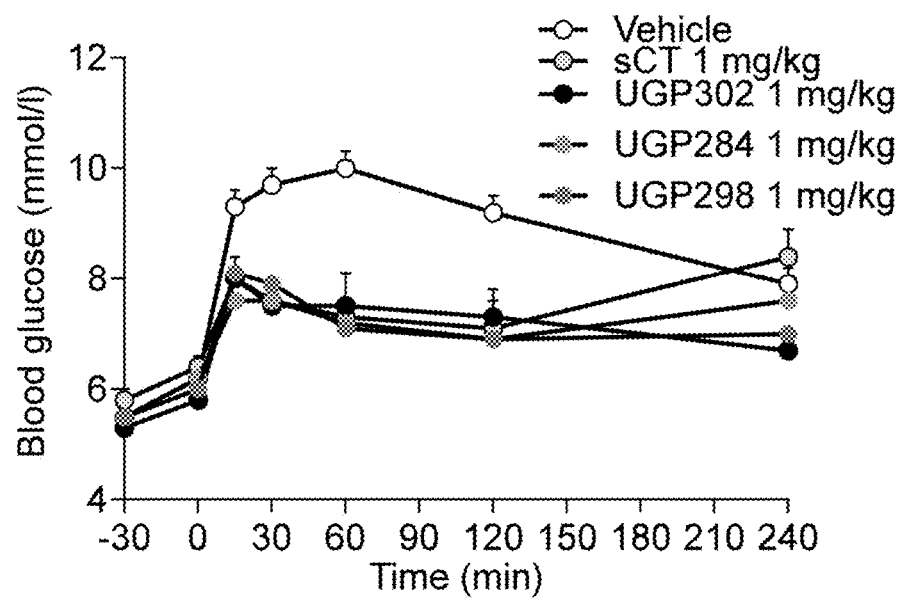
Figure 10D:
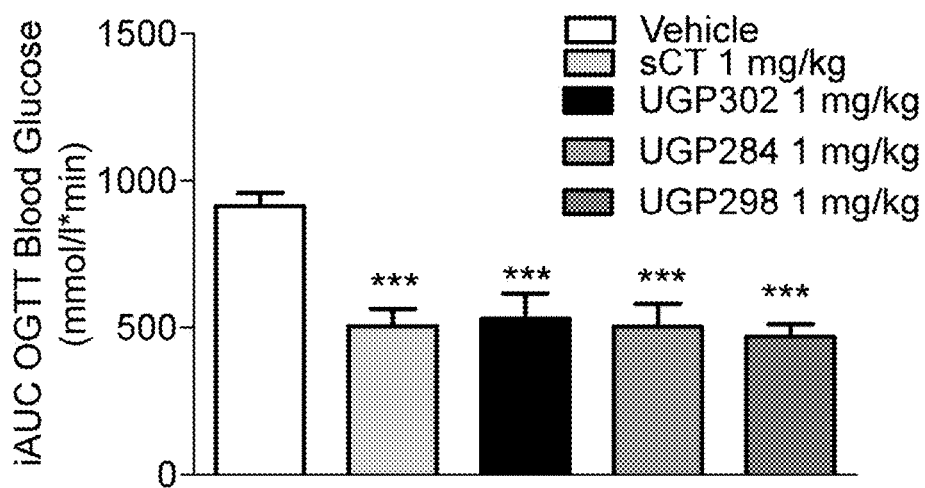
Figure 10E:
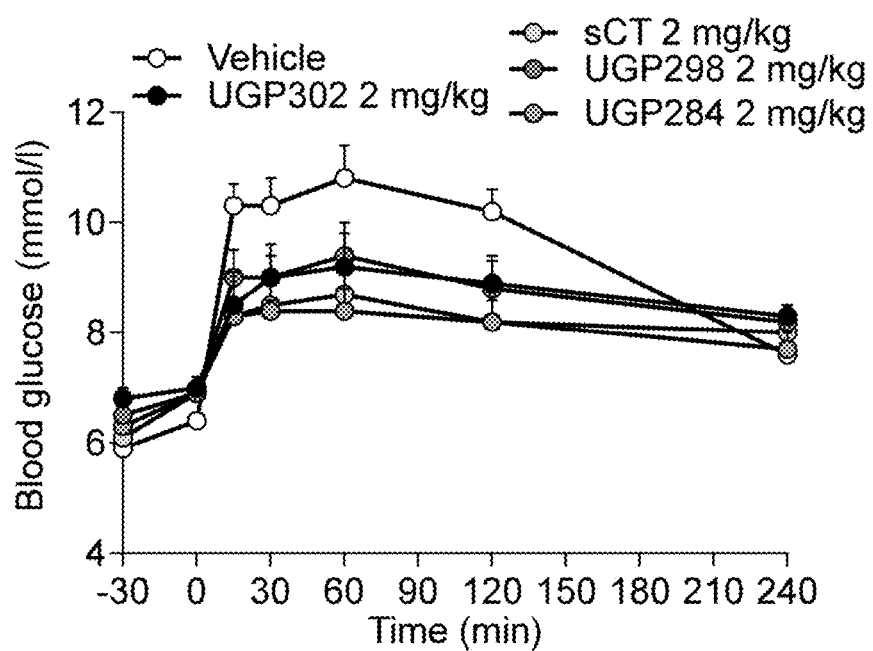
Figure 10F:
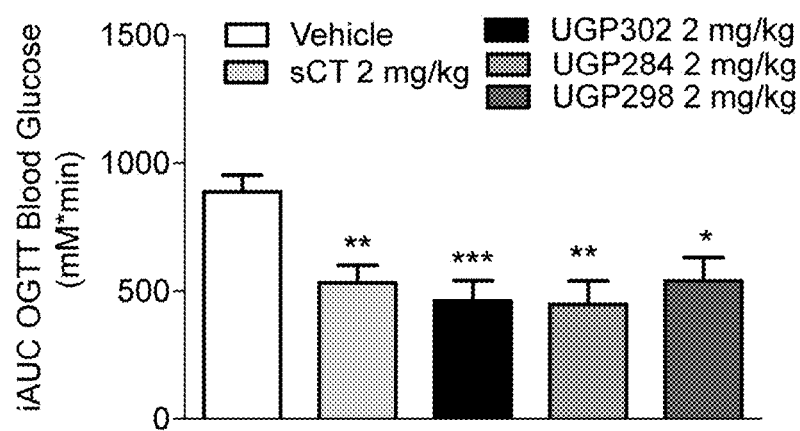

Three different doses of oral sCT/calcitonin mimetic 1 containing 0.5, 1 and 2 mg/kg compound were applied by gavage twice daily to 4 groups of rats for 3 days prior to OGTT. The experimental set-up was a cross-over design. * $P<0.05$,  $P<0.01$, * $P<0.001$ vs oral vehicle. Results are presented in FIGS. 7A-7B and FIGS. 8A-8B as means±SEM. FIG. 7A and FIG. 7B show the effect of oral sCT versus oral UGP 302 at a first dosage on glucose tolerance during OGTT in DIO rats as measured in Example 2. FIG. 8A and FIG. 8B show the effect of oral sCT versus oral UGP 302 at a second dosage on glucose tolerance during OGTT in DIO rats as measured in Example 2.

Oral sCT significantly reduced glucose iAUC during OGTT for 0.5, 1 and 2 mg/kg doses compared to oral vehicle, thus confirming the postprandial glycemic control exerted by oral application of sCT as previously demonstrated. Calcitonin mimetic 1 demonstrated a similar significantly reduction in iAUC as observed for oral sCT, although with no clear superiority to oral sCT within the various UGPs.

EXAMPLE 3

Acute and Short Term Effects of Oral sCT Versus UGP284, UGP298 and UGP302

Animals

The study was performed in male Levin-DIO rats (diet-sensitive) and Levin-DR (diet-resistant) (TacLevin: CD (SD) D10) (Taconic, Hudson, N.Y., U.S.A.) obtained at age 6-7 weeks. On arrival, DIO rats were given high fat diet (60 kcal %) (#D12495, Research Diets Inc., New Brunswick, N.J., USA) and kept on the same diet for 12 weeks prior to and during the experiment. DR rats were given low-fat diet and served as control group. Animals were pair-wise housed throughout the study. Rats were handled and pre-dosed once daily with MilliQ H2O for 2-3 weeks prior to experimental start to reduce stress-induced hyperglycemia. On the day prior to study start animals were given a single dose of vehicle. Baseline parameters were recorded in an overnight fasting (16 h) condition. Rats were randomized into treatment groups based on fasting body weight (BW) and fasting plasma glucose (FPG). Body weight, food and water intake were recorded prior to and at study end.

Compound

Oral sCT/UGP solution was prepared on the day of dosing by mixing the carrier with the given compound based on the following calculations:

5-CNAC (Vehicle):

Animals treated with oral 5-CNAC received a dose of 150 mg/kg dissolved in milliQ H20.
Dosage-level for 5-CNAC: 150 mg/kg
Dosing volume: 5 ml/kg
Compound concentration: 30 mg/ml
(sCT/UGP284/UGP298/UGP302)

Animals treated with oral sCT or oral UGP284/UGP298/UGP302 received doses of 0.5 mg/kg, 1.0 mg/kg or 2.0 mg/kg combined with 150 mg/kg 5-CNAC—all dissolved in milliQ $H_2O$.
Dosage-level for sCT/UGP284/UGP298/UGP302: 0.5 mg/kg
Dosing volume: 5 ml/kg
Compound concentration: 0.1 mg/ml
Dosage-level for sCT/UGP284/UGP298/UGP302: 1.0 mg/kg
Dosing volume: 5 ml/kg
Compound concentration: 0.2 mg/ml
Dosage-level for sCT/UGP284/UGP298/UGP302: 2.0 mg/kg
Dosing volume: 5 ml/kg
Compound concentration: 0.4 mg/ml Drug administration were given by per oral (p.o.) gavage b.i.d. during the study period and as single dose in the morning prior to start of OGTT.

Oral gavage of glucose during OGTT was prepared by the following calculation:
D-Glucose:
Animals were given 2 g/kg single dose dissolved in milliQ H20.
Dosage-level for D-Glucose: 2 g/kg
Dosing volume: 4 ml/kg
Compound concentration: 500 mg/ml
Experimental Setup
Acute Testing—Treatment Period for 0.5 mg/kg, 1 mg/kg and 2 mg/kg:

| Day 0 | Day 1-2 | Day 3 | Day 4 | Day 5 | Day 6 | Day 7 |
|---|---|---|---|---|---|---|
| $1^{st}$ OGTT All vehicle | Rest No handling | Pre-dose All vehicle | Treatment (b.i.d) | Treatment (b.i.d) | Treatment (b.i.d) | $2^{nd}$ OGTT Single dose |

Following the initial ($1^{st}$) OGTT, animals were randomized into treatment groups based on FBG and BW. Animals were pre-treated 3 days (b.i.d.) prior to $2^{nd}$ OGTT.
The study was performed in an x-over design with each animal being its own control.
OGTT Following Overnight Fasting (16 h):

| −30 | 0 | 15 | 30 | 60 | 120 | 240 min |
|---|---|---|---|---|---|---|
| D B BG | G B BG | B BG | B BG | B BG | B BG | B BG |

D = Drug;
BG = Blood glucose;
B = Blood;
G = Glucose

Blood sampling and glycemia were measured by heated tail venous puncture. Whole blood glucose levels were determined with an ACCU-CHEK® Avia blood glucose meter (Roche Diagnostics, Rotkreuz, Switzerland). Blood (approx 300 μl) is collected in 1 ml MiniCollect K3EDTA plasma-tube (Greiner-Bio-One GmbH, Frickenhausen, Germany), inverted, and stored on ice. Tubes are centrifuged 3000×g (5000 rpm in table centrifuge) for 10 min at 4° C. and plasma obtained. Plasma samples are stored at −20° C. until analysis. A total of ~2.5 ml blood is obtained during OGTT (~0.3% of body weight).

Experimental Groups:

| Intervention | Compound | Conc. | Number |
|---|---|---|---|
| Oral vehicle | 5-CNAC | 150 mg/kg | (4 groups of n = 8) X-over design to 0.5 mg/kg |
| Oral sCT | 5-CNAC + sCT | 150 mg/kg + 0.5 mg/kg | n = 8 |
| Oral UGP284 | 5-CNAC + UGP284 | 150 mg/kg + 0.5 mg/kg | n = 8 |
| Oral UGP298 | 5-CNAC + UGP298 | 150 mg/kg + 0.5 mg/kg | n = 8 |
| Oral UGP302 | 5-CNAC + UGP302 | 150 mg/kg + 0.5 mg/kg | n = 8 |
| Oral vehicle | 5-CNAC | 150 mg/kg | (4 groups of n = 8) X-over design to 1 mg/kg |
| Oral sCT | 5-CNAC + sCT | 150 mg/kg + 1 mg/kg | n = 8 |
| Oral UGP284 | 5-CNAC + UGP284 | 150 mg/kg + 1 mg/kg | n = 8 |
| Oral UGP298 | 5-CNAC + UGP298 | 150 mg/kg + 1 mg/kg | n = 8 |
| Oral UGP302 | 5-CNAC + UGP302 | 150 mg/kg + 1 mg/kg | n = 8 |
| Oral vehicle | 5-CNAC | 150 mg/kg | (4 groups of n = 8) X-over design to 2 mg/kg |
| Oral sCT | 5-CNAC + sCT | 150 mg/kg + 2 mg/kg | n = 8 |
| Oral UGP284 | 5-CNAC + UGP284 | 150 mg/kg + 2 mg/kg | n = 8 |
| Oral UGP298 | 5-CNAC + UGP298 | 150 mg/kg + 2 mg/kg | n = 8 |
| Oral UGP302 | 5-CNAC + UGP302 | 150 mg/kg + 2 mg/kg | n = 8 |

Statistics

Statistical analysis was performed by one-way ANOVA followed by the Dunnett's post hoc test for multiple comparison. Student's t-test was performed to compare two paired group. All analysis was performed using GRAPHPAD PRISM software (GraphPad Prism, San Diego, Calif. U.S.A). Incremental area under curve (iAUC) during OGTT was calculated by the trapezoidal method. A value of $P<0.05$ was considered to be significant. All data are presented as mean±standard error of the mean (SEM).

Results

Baseline Characteristics

The 12-weeks ad libitum high-fat diet induced a pronounced obese phenotype in the diet-sensitive (D10) rats when comparing body weight to their diet-resistant (DR) littermates ($P<0.001$) (Table 5). Fasting glycemia was not different between DIO and DR. In contrast, area under curve (AUC) calculations during OGTT were significantly higher in DIO rats compared to DR rats, demonstrating the high-fat diet-induced glucose intolerance (Table 5).

TABLE 5

Metabolic parameters in DIO and DR rats

|  | Diet-resistant (DR) | Diet-sensitive (DIO) |
|---|---|---|
| Body Weight (g) | 609.5 ± 24.5 | 813.6 ± 9.8*** |
| Fasting plasma glucose (mM) | 5.8 ± 0.1 | 5.8 ± 0.2 |

TABLE 5-continued

Metabolic parameters in DIO and DR rats

| | Diet-resistant (DR) | Diet-sensitive (DIO) |
|---|---|---|
| AUC in OGTT Blood glucose (mM*min) | 648.8 ± 27.3 | 888.4 ± 64.3*** |

AUC, area under curve; OGTT, oral glucose tolerance test.
Data are means ± SEM (n = 12/DR, n = 24/DIO).

Body Weight and Food Intake

Oral sCT dose-dependently decreased body weight and food intake following the short-term treatment period and thus confirmed the anorectic action induced by targeting the amylin receptor as previously observed. In general, all UGP mimetics demonstrated dose-dependently superiority to oral sCT in regards to reduction in body weight as illustrated in FIGS. 9A-9F. Application of UGP302 at 0.5 mg/kg demonstrated significantly difference to oral sCT 0.5 mg/kg. For UGP284, significantly difference at 2 mg/kg dose was observed when compared to oral sCT 2 mg/kg. Finally, UGP298 at both 1 mg/kg and 2 mg/kg doses were significantly different when compared with oral sCT at similar doses. FIG. 9A, FIG. 9B, FIG. 9C, FIG. 9D, FIG. 9E, and FIG. 9F show the effect of three different doses of oral sCT/UGP284/UGP298/UGP302 containing 0.5, 1 and 2 mg/kg compound were applied by gavage twice daily to 4 groups of rats for 3 days. * $P<0.05$, ** $P<0.01$ vs oral sCT. Results are presented as means±SEM.

Glucose Tolerance

FIG. 10A, FIG. 10B, FIG. 10C, FIG. 10D, FIG. 10E, and FIG. 10F show the effect of oral sCT versus oral UGPs on glucose tolerance during OGTT in DIO rats. Three different doses of oral sCT/UGP284/UGP298/UGP302 containing 0.5, 1 and 2 mg/kg compound were applied by gavage twice daily to 4 groups of rats for 3 days prior to OGTT. The experimental set-up was a cross-over design. * $P<0.05$,  $P<0.01$, * $P<0.001$ vs oral vehicle. Results are presented as means±SEM. All UGPs demonstrated a similar significant reduction in iAUC as observed for oral sCT.

In conclusion, application of UGP284, UGP298 and UGP302 at 0.5, 1 and 2 mg/kg doses demonstrated superiority to equivalent doses of oral sCT in regards to energy balance in male DIO rats. Furthermore, UGP284, UGP298 and UGP302 at doses of 0.5, 1 and 2 mg/kg produced an improvement in glucose tolerance during OGTT.

EXAMPLE 4

Binding of sCT Analogs to T47D Cell Calcitonin Receptors sCT analogs at various concentrations were tested in a T47D (human breast epithelial cell line) bioassay. This cell line is known to have the following receptors: calcitonin, androgen, progesterone, glucocrticoid, prolactin and estrogen. The results are presented in FIG. 11 as % cAMP binding relative to sCT which was set at 100% cAMP binding at a concentration of 1000 pg/mL. It can be seen that UGP302 provides the highest level of binding of all the tested compounds and that it provides a higher level of binding than sCT.

EXAMPLE 5

Food Consumption and Weight Change in Rats Fed sCT Analogs

Male Sprague-Dawley rats were housed individually in cages in which the light/dark cycle was reversed. Rats were allowed to eat ad libitum. Food consumption and rat weights were monitored daily during each study. Rats were injected intramuscularly with a saline placebo or the indicated peptide at the specified dose in saline. The data in the following tables is summarized as the mean change in food consumption relative to the day before treatment began (day −1) and as the mean change in weight relative to the day before treatment began.

Figures 13A, 13B:
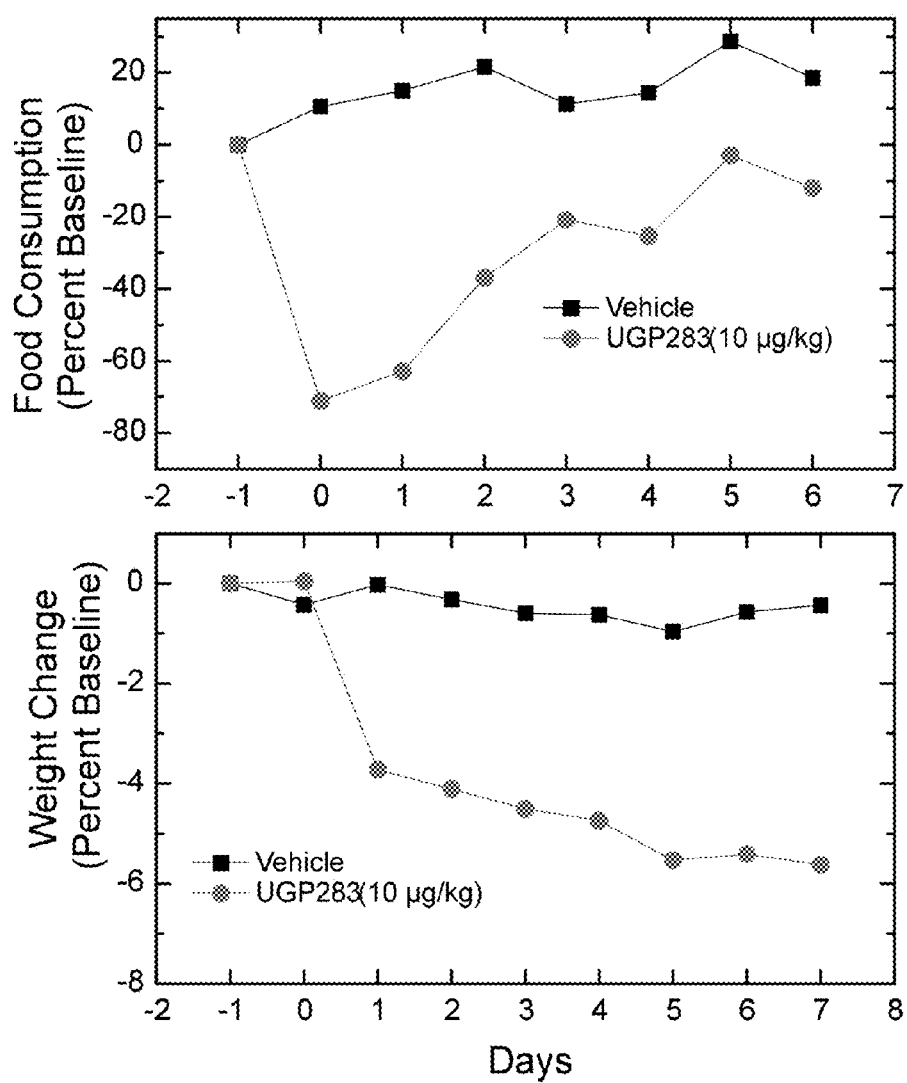
FIG. 13A and FIG. 13B show food consumption (FIG. 13A) and weight change measurements (FIG. 13B) for UGP 283 as measured in Example 5.
Figures 14A, 14B:
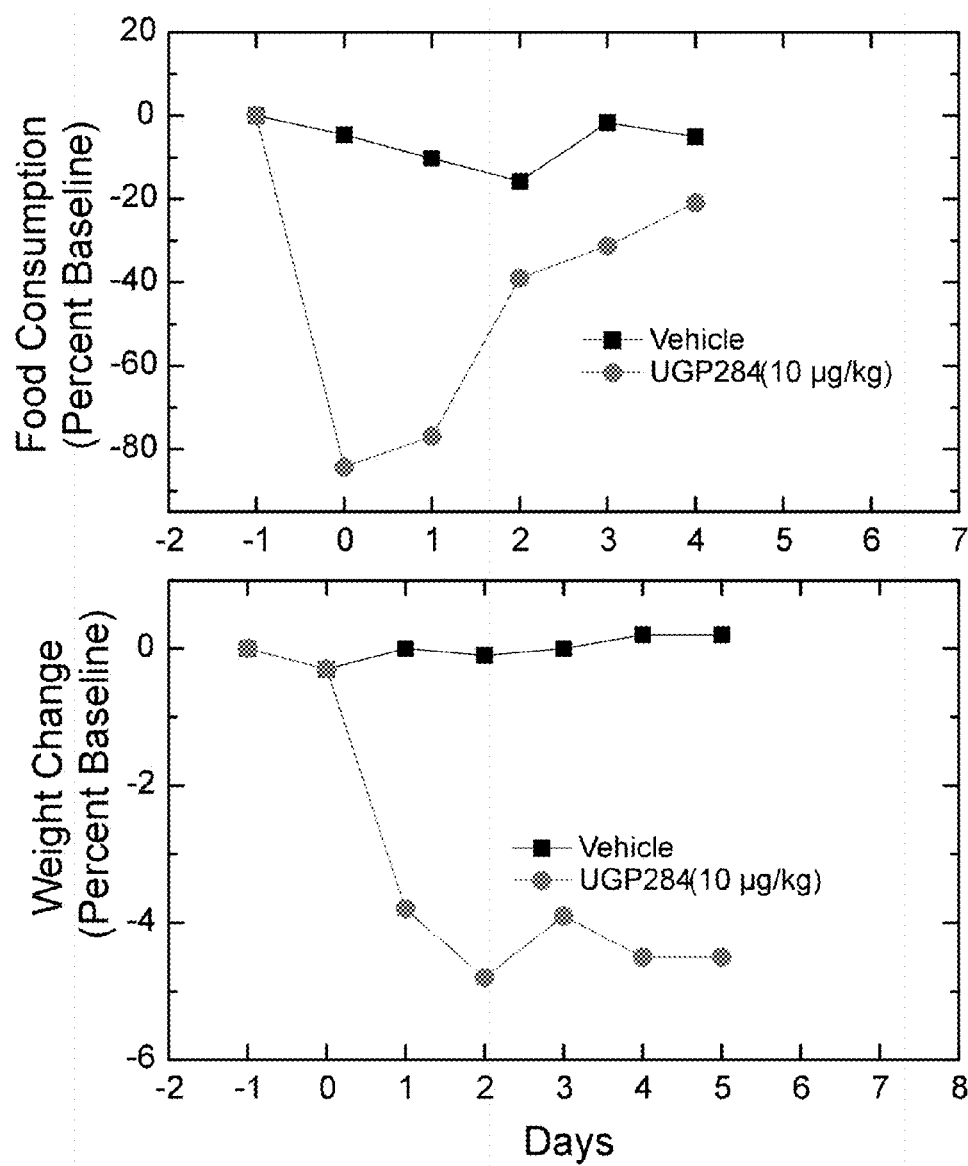
FIG. 14A and FIG. 14B show food consumption (FIG. 14A) and weight change measurements (FIG. 14B) for UGP 284 as measured in Example 5.
Figures 15A, 15B:
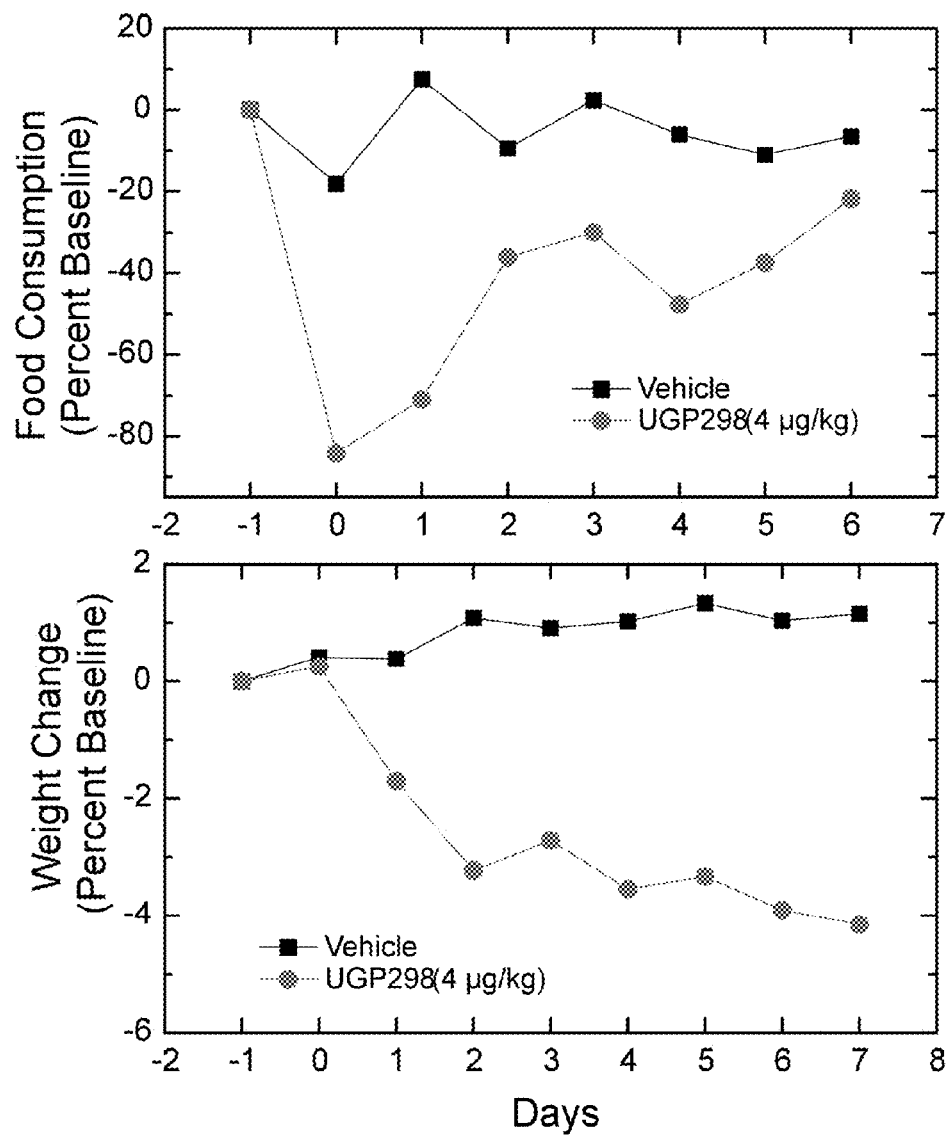
FIG. 15A and FIG. 15B show food consumption (FIG. 15A) and weight change measurements (FIG. 15B) for UGP 298 as measured in Example 5.
Figure 16A:
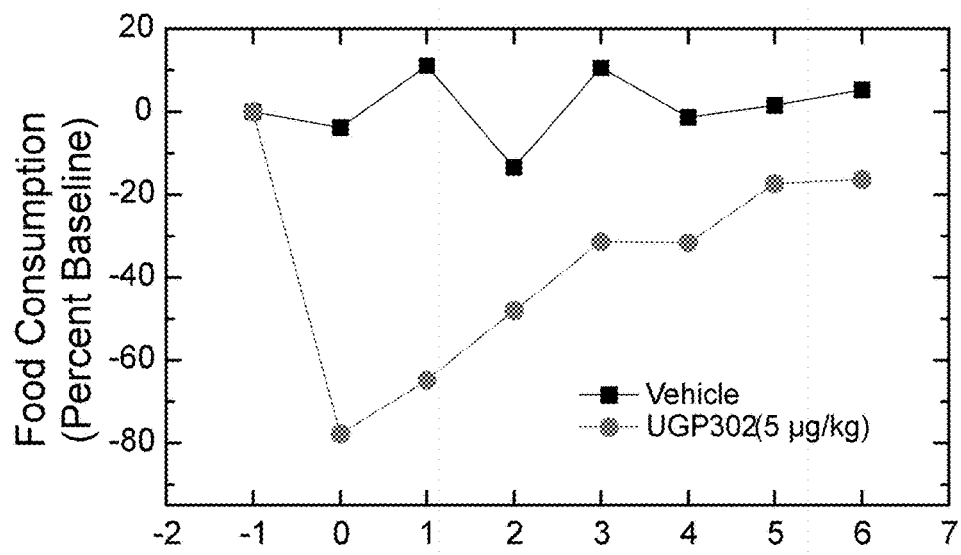
FIG. 16A and FIG. 16B show food consumption (FIG. 16A) and weight change measurements (FIG. 16B) for UGP 302 as measured in Example 5.
Figure 16B:
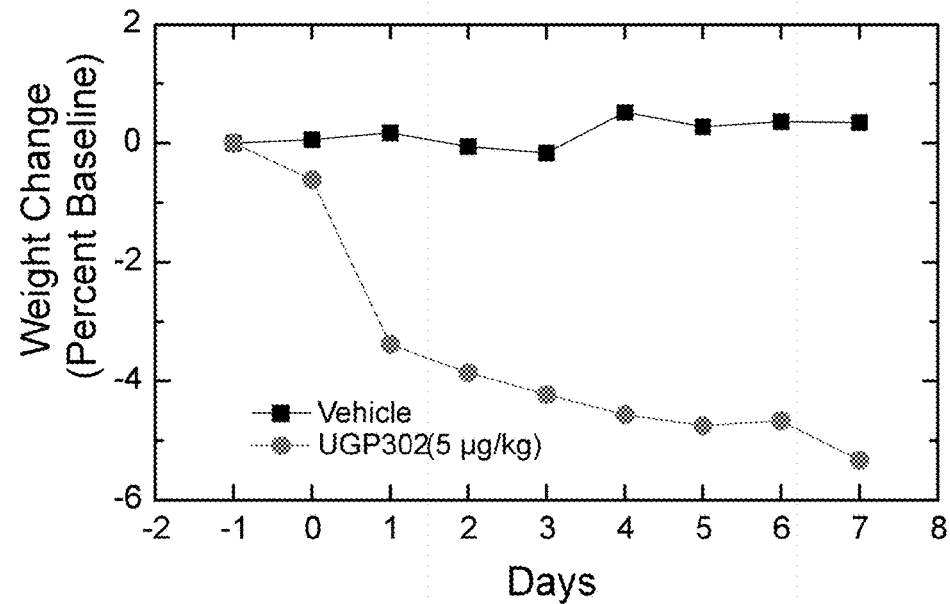
Figure 17A:
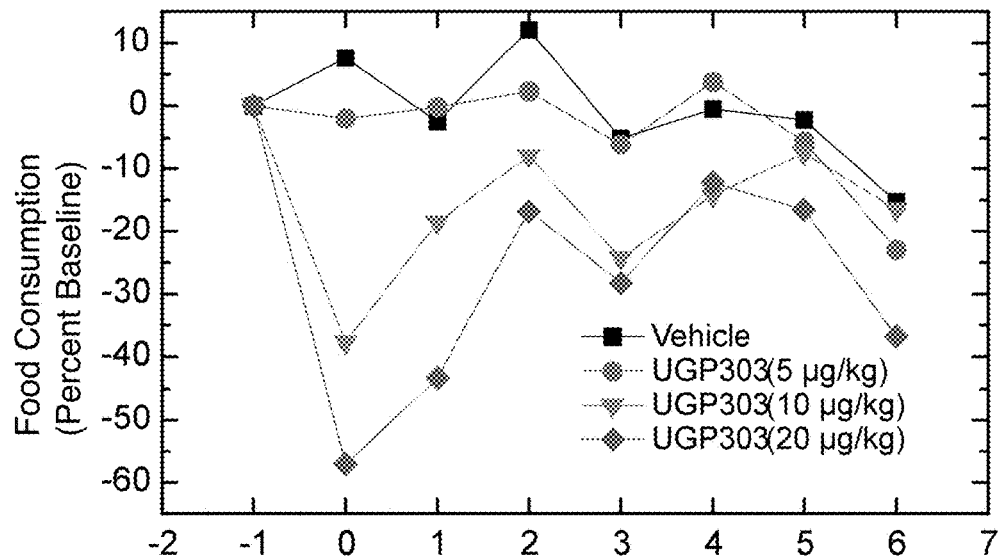
FIG. 17A and FIG. 17B show food consumption (FIG. 17A) and weight change measurements (FIG. 17B) for UGP 303 as measured in Example 5.
Figure 17B:
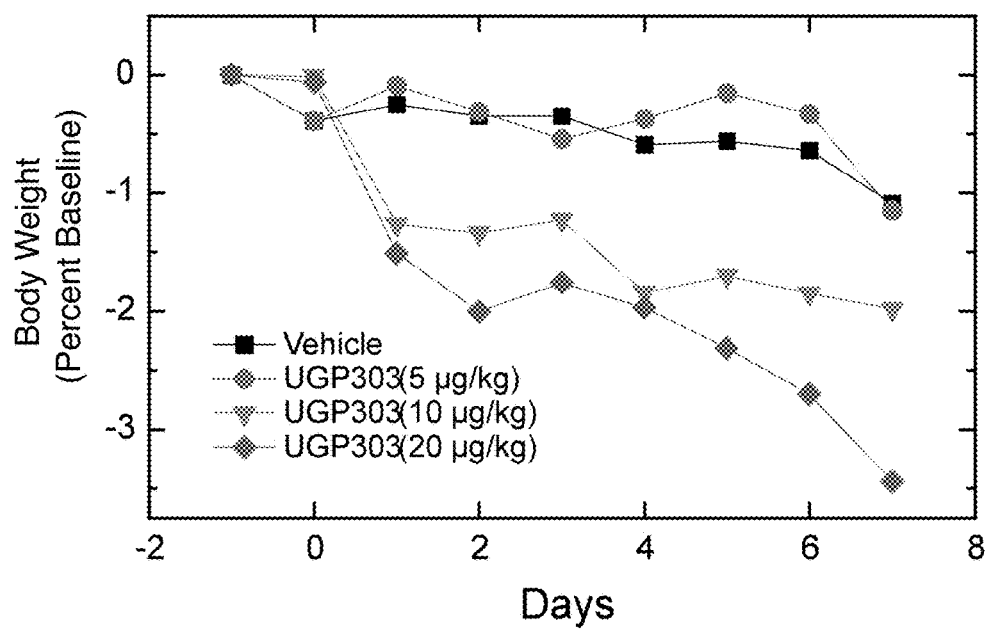

The results are shown in FIGS. 12A-12B, 13A-13B, 14A-14B, 15A-15B, 16A-16B, and 17A-17B. FIG. 12A and FIG. 12B show food consumption and weight change measurements, respectively, for UGP 282 as measured in Example 5. FIG. 13A and FIG. 13B show food consumption and weight change measurements, respectively, for UGP 283 as measured in Example 5. FIG. 14A and FIG. 14B show food consumption and weight change measurements, respectively, for UGP 284 as measured in Example 5. FIG. 15A and FIG. 15B show food consumption and weight change measurements, respectively, for UGP 298 as measured in Example 5. FIG. 16A and FIG. 16B show food consumption and weight change measurements, respectively, for UGP 302 as measured in Example 5. FIG. 17A and FIG. 17B show food consumption and weight change measurements, respectively, for UGP 303 as measured in Example 5.

It can be seen that all of the tested compounds induce weight loss and reduce feed intake.

EXAMPLE 6

Markers of Osteoporosis and Osteoarthritis

The effect of sCT/calcitonin mimetic on bone and cartilage loss was studied in DIO rats. The animals were dosed as described in Table 6 below, and 2 hours after treatment blood sampling was done by heated tail venous puncture.

Serum CTX-I levels, as an indication of bone resorption, were measured using the RatLaps™ ELISA, and serum CTX-II levels, as an indication of cartilage degradation, were measured using the Serum PC Cartilaps™ ELISA.

TABLE 6

Experimental groups

| Intervention | Compound | Conc. | Number |
|---|---|---|---|
| Oral vehicle | 5-CNAC | 150 mg/kg | n = 8 |
| Oral sCT | 5-CNAC + sCT | 150 mg/kg + 1 mg/kg | n = 8 |
| Oral calcitonin mimetic of SEQ ID NO: 18 | 5-CNAC + SEQ ID NO: 15 | 150 mg/kg + 1 mg/kg | n = 8 |

Figure 18:
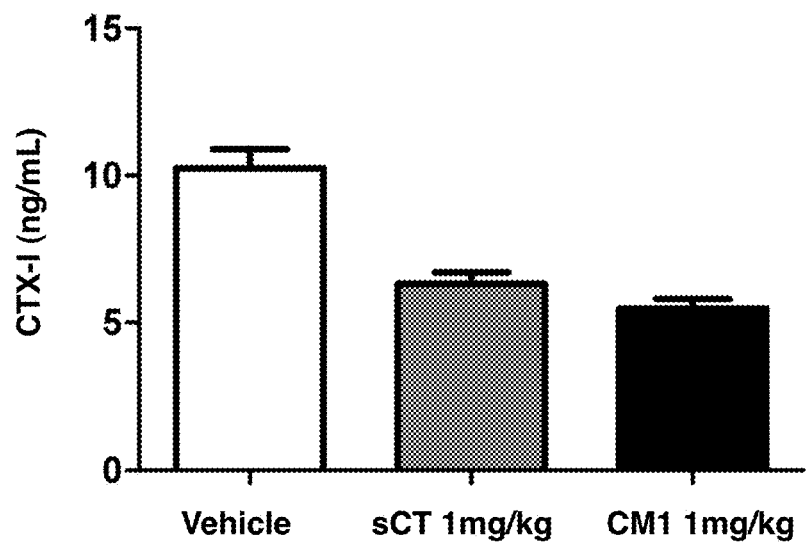
FIG. 18 shows the reduction of bone resorption produced by treatment with UGP302 in rats.
Figure 19:
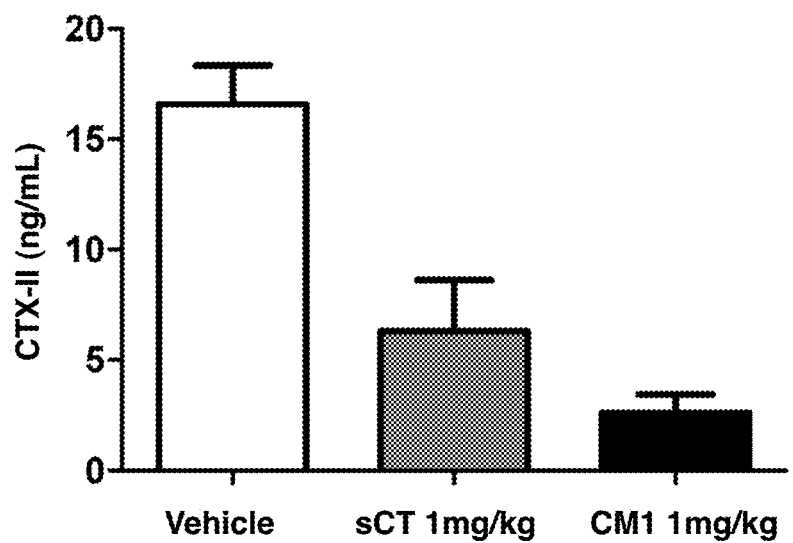
FIG. 19 shows cartilage resorption produced by treatment with UGP302 in rats.

The results are seen in FIG. 18 and FIG. 19, where a calcitonin mimetic of SEQ ID NO: 18 shows a stronger effect in reduction of both bone resorption and cartilage degradation than does sCT.

In some embodiments, a peptide of the present disclosure has a sequence selected from SEQ ID NO: 11, SEQ ID NO: 12, SEQ ID NO: 13, SEQ ID NO: 14, SEQ ID NO: 15, SEQ ID NO: 17 and SEQ ID NO: 18.

In some embodiments, a method includes administering to a patient an effective amount of a peptide selected from the group consisting of: SEQ ID NO: 11, SEQ ID NO: 12, SEQ ID NO: 13, SEQ ID NO: 14, SEQ ID NO: 15, and SEQ ID NO: 17 to affect a weight reduction in the patient.

In some embodiments, a method includes administering to a patient an effective amount of a peptide selected from the group consisting of: SEQ ID NO: 11, SEQ ID NO: 12, SEQ ID NO: 13, SEQ ID NO: 14, SEQ ID NO: 15, and SEQ ID NO: 17 to affect postprandial glycemic control in the patient.

In some embodiments, a method includes administering to the patient an effective amount of a peptide selected from the group consisting of: SEQ ID NO: 11, SEQ ID NO: 12, SEQ ID NO: 13, SEQ ID NO: 14, SEQ ID NO: 15, and SEQ ID NO: 17 to affect an improvement in glycemic control in the patient.

In some embodiments, a method includes administering to a patient an effective amount of a peptide of SEQ ID NO: 18 having the sequence $C_m$SNLSTCVLGKLSQELH KLQ-TYPRTDVGANXaaXaa$_a$ so as to reduce at least one of bone resorption and cartilage degradation in the patient.

EXAMPLE 7

Combination Treatment with Metformin

To assess the potential of UGP302 (SEQ ID NO: 15) in combination with metformin, Zucker Diabetic Fatty rats were used. At the age of 6 weeks 40 rats were randomized into four groups according to HbA1c, FPG and BW. The groups were: Control (Vehicle), Metformin 400 mg/kg/day, UGP302 5 μg/kg/day and the combination of the two molecules in the stated respective amounts. The treatments were given once daily, and metformin was dosed orally, while UGP302 was given subcutaneously, and the animals were treated for 8 weeks. Fasting blood glucose (FPG) and non-fasted blood glucose (PPG) were monitored biweekly, while HbA1c was measured at termination.

Figure 20:
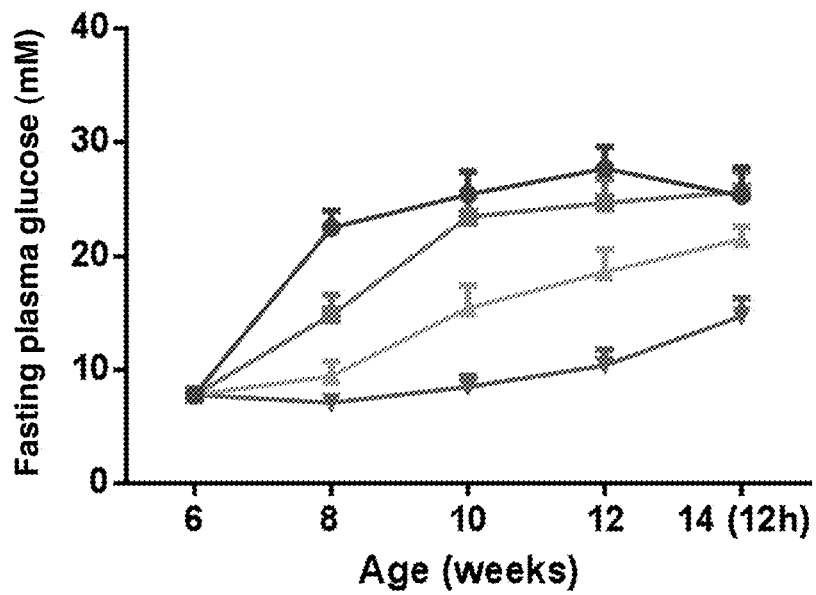
FIG. 20 shows results obtained in Example 7 showing fasting blood glucose (FBG) of tested rats.
Figure 21:
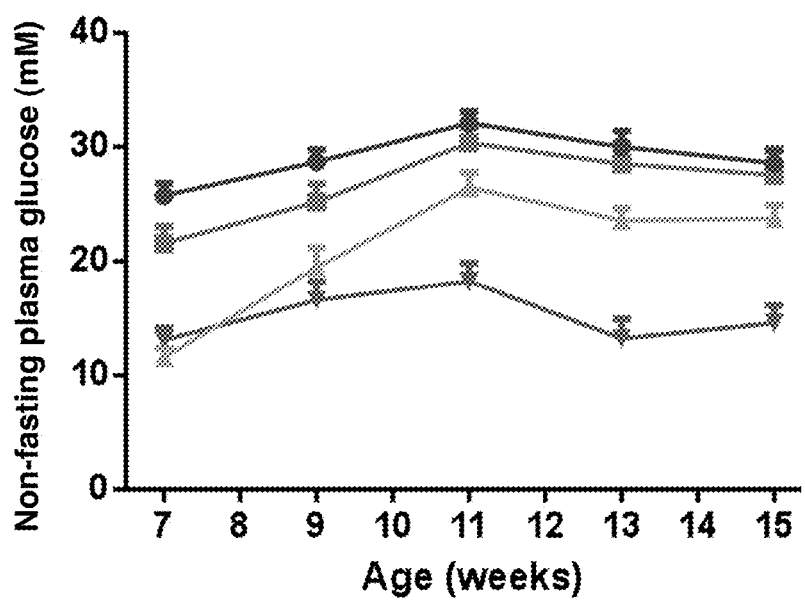
FIG. 21 shows results obtained in Example 7 showing non-fasted blood glucose (PPG) of subject rats.
Figure 22:
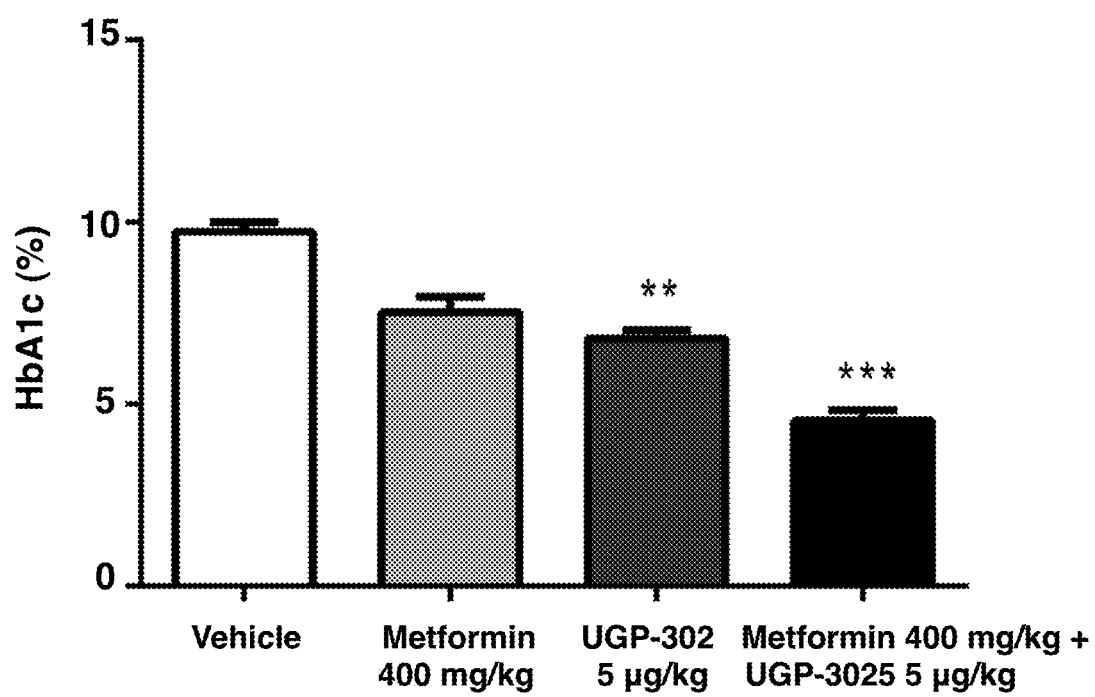
FIG. 22 shows results obtained in Example 7 showing HbA1c levels of subject rats.

As can be seen in FIGS. 20, 21 and 22, both metformin and UGP302 alone reduced both FPG and PPG, with UGP302 providing a pronounced reduction throughout the study, while metformin lost the ability to control blood glucose with time. In the combination group, a markedly superior response was observed in both FPG and PPG, clearly showing that these molecules work as adjunct therapies. This synergistic effect is also seen in the HbA1c levels, where the combination leads to a superior improvement when compared to both vehicle and either molecule alone. Particularly notably, the superior effect of the combination as compared to UGP302 alone persisted throughout the test, even though the individual effect of metformin did not.

Figure 23A:
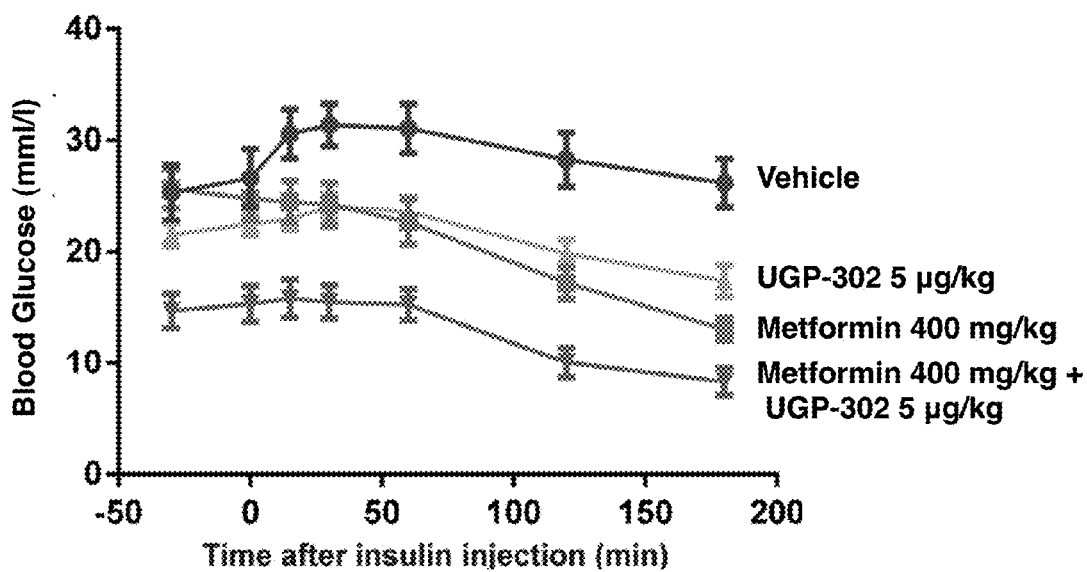
FIG. 23A and FIG. 23B show results obtained in Example 7 showing the results of oral glucose tolerance tests (OGTT) as plots of blood glucose against time (FIG. 23A) and as total Area Under Curve tAUC measurements (FIG. 23B).
Figure 23B:
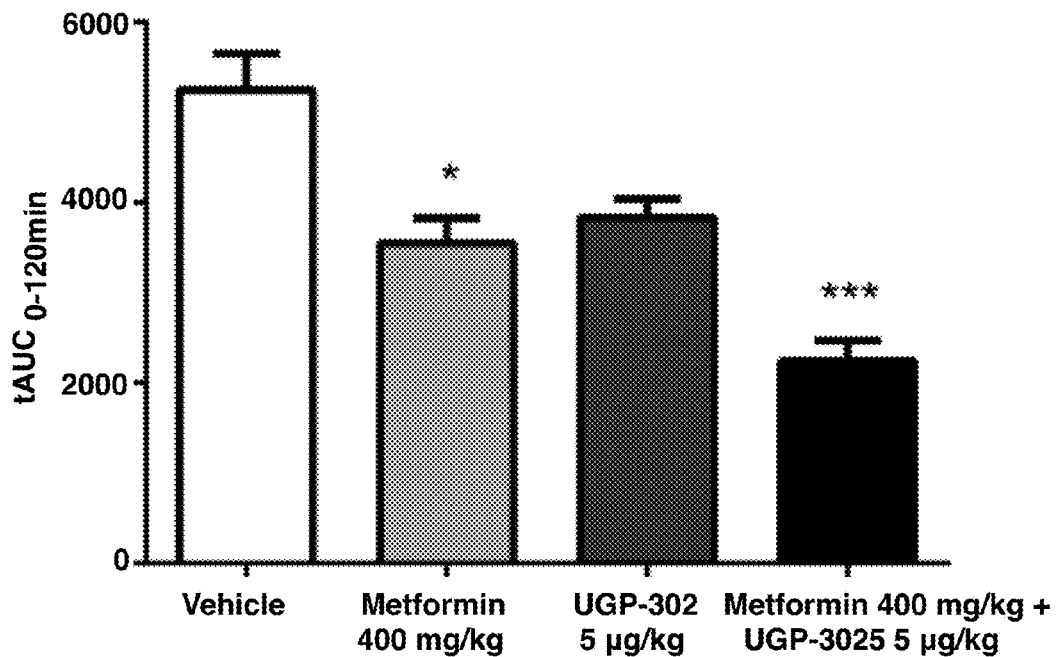
Figure 24A:
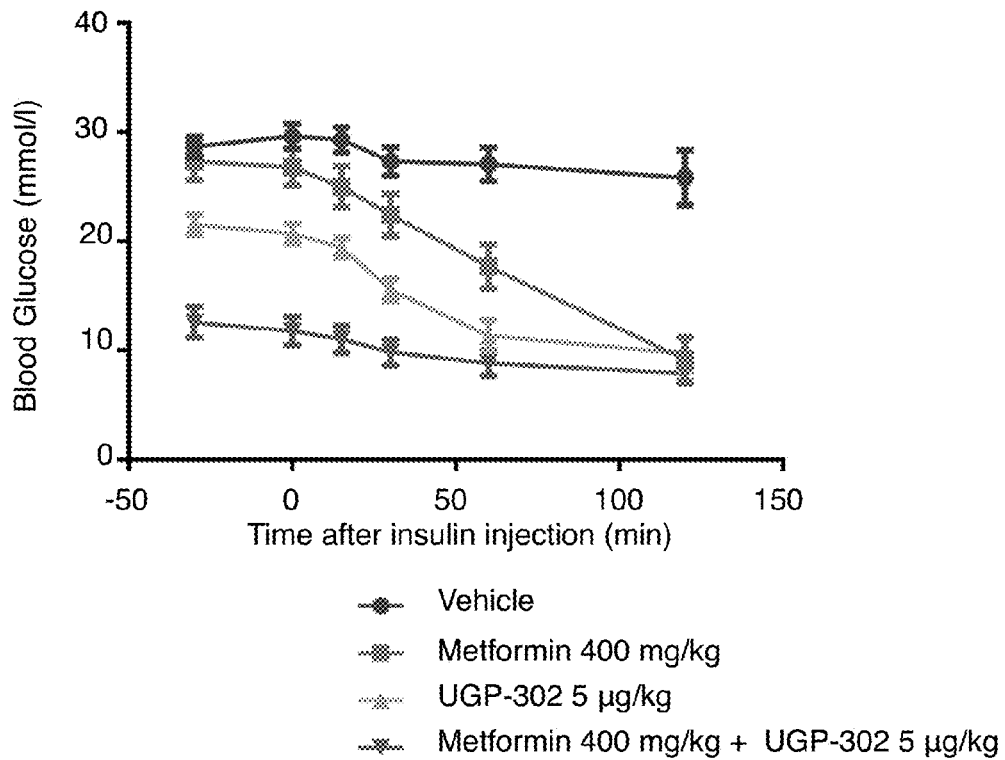
FIG. 24A and FIG. 24B show results obtained in Example 7 showing the results of insulin tolerance tests (IPITT) as plots of blood glucose against time (FIG. 24A) and as total Area Under Curve tAUC measurements (FIG. 24B).
Figure 24B:
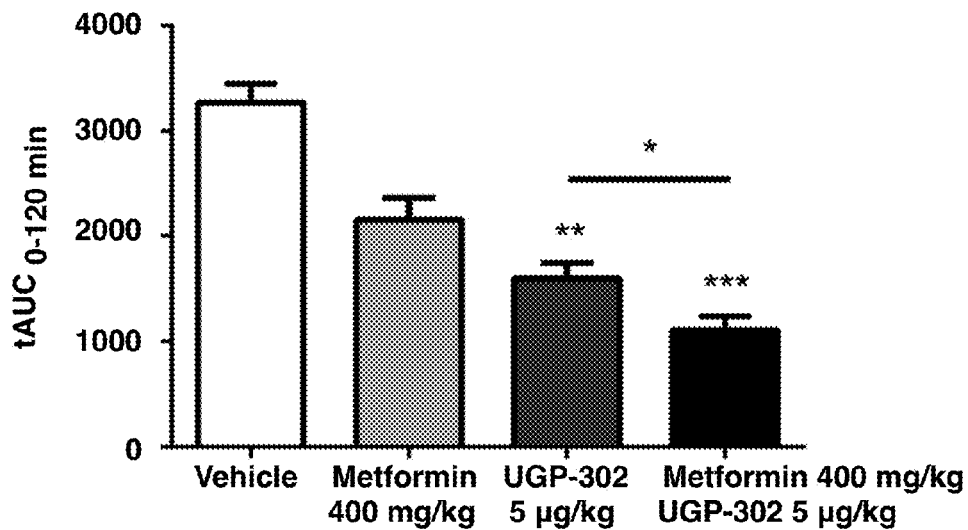

To further assess the effect of both single doses of each molecule and the combination of these at those same doses, the rats underwent an oral glucose tolerance test (OGTT) and an insulin tolerance test (ITT). In these tests the activity of both molecules is apparent, as they individually improve both glucose and insulin tolerance. However, the combination of UGP302 and metformin was superior to either molecule alone, both in terms of glucose tolerance and insulin tolerance (FIGS. 23A-23B), clearly indicating the benefit of the combination.

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A method for treating type I diabetes, type II diabetes, metabolic syndrome, or obesity, or appetite suppression, or for mitigating insulin resistance, or for improving glycemic control, or for improving serum insulin level control in a patient in need of such treatment, comprising administering to the patient as a combination therapy an effective amount of an insulin sensitizer and of a peptide selected from the group consisting of SEQ ID NO: 12, SEQ ID NO: 15, SEQ ID NO: 17, SEQ ID NO: 19, SEQ ID NO: 22, and SEQ ID NO: 24.

2. The method of claim 1, wherein the peptide is selected from the group consisting of:
R-CSNLSTCVLGKLSQELHKLQTYPRTDVGANAP-NH2 SEQ ID NO: 19, and
R-CSNLSTCVLGKLSQELHKLQTYPRTDVGANAY-NH2 SEQ ID NO: 24;
wherein each peptide R is absent or is an acylation moiety.

3. The method of claim 1, wherein the peptide is selected from the group consisting of:
AcCSNLSTCVLGKLSQELHKLQTYPRTDVGANAP-NH2 SEQ ID NO: 15, and
SuccCSNLSTCVLGKLSQELHKLQTYPRTDV-GANAY-NH2 SEQ ID NO: 17.

4. The method of claim 1, wherein the peptide is formulated for enteral administration.

5. The method of claim 1, wherein the peptide is formulated for parenteral administration.

6. The method of claim 1, wherein the peptide is formulated with a carrier for oral administration.

7. The method of claim 6, wherein the carrier comprises N-(5-chlorosalicyloyl)-8-aminocaprylic acid (5-CNAC), sodium salt of 10-(2-Hydroxybenzamido)decanoic acid (SNAD), or sodium salt of N-(8-[2-hydroxybenzoyl]amino) caprylic acid (SNAC).

8. The method of claim 1, wherein the peptide is formulated in a pharmaceutical composition for oral administration comprising coated citric acid particles, and wherein the coated citric acid particles increase the oral bioavailability of the peptide.

9. The method of claim 1, wherein said treatment is for effecting a weight reduction of the patient.

10. The method of claim 1, wherein the treatment is to improve postprandial glycemic control in the patient.

11. The method of claim 1, wherein the insulin sensitiser is at least one selected from the group consisting of a biguanide, a thiazolidinedione, a dual peroxisome proliferator-activated receptor (PPAR) agonist, a sulphonylurea, a meglitinide/glinide, a glucagon-like peptide-1 (GLP-1) analog, a dipetidyl peptidase 4 (DPP-4) inhibitor, an insulin analog, an alpha-glucosidase inhibitor, an amylin analog, a sodium/glucose cotransporter 2 (SGLT2) inhibitor, benfluorex, and tolrestat.

12. The method of claim 11, wherein the biguanide is selected from the group consisting of metformin, buformin and phenformin.

13. The method of claim 11, wherein the thiazolidinedione is selected from the group consisting of balaglitazone, pioglitazone, rivoglitazone, rosiglitazone and troglitazone.

14. The method of claim 11, wherein the dual peroxisome proliferator-activated receptor (PPAR) agonist is selected from the group consisting of aleglitazar, muraglitazar and tesaglitazar.

15. The method of claim 11, wherein the sulphonylurea is selected from the group consisting of carbutamide, chloropropamide, gliclazide, tolbutamide, tolazamide, glipizide, glibenclamide, glyburide, gliquidone, glyclopyramide and glimepriride.

16. The method of claim 11, wherein the meglitinide/glinide is selected from the group consisting of nateglinide, repaglinide and mitiglinide.

17. The method of claim 11, wherein the glucagon-like peptide-1 (GLP-1) analog is selected from the group consisting of exenatide, liraglutide and albiglutide.

18. The method of claim 11, wherein the dipetidyl peptidase 4 (DPP-4) inhibitor is selected from the group consisting of alogliptin, linagliptin, saxagliptin, sitagliptin and vildagliptin.

19. The method of claim 11, wherein the alpha-glucosidase inhibitor is selected from the group consisting of acarbose, miglitol and voglibose.

20. The method of claim 11, wherein the amylin analog is pramlintide.

21. The method of claim 11, wherein the sodium/glucose cotransporter 2 (SGLT2) inhibitor is selected from the group consisting of dapagliflozin, remogliflozin and sergliflozin.

22. The method of claim 1, wherein the insulin sensitizer is metformin.

* * * * *

SEQUENCE LISTING

<160> NUMBER OF SEQ ID NOS: 24

<210> SEQ ID NO 1
<211> LENGTH: 32
<212> TYPE: PRT
<213> ORGANISM: salmon

<400> SEQUENCE: 1

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 2
<211> LENGTH: 32
<212> TYPE: PRT
<213> ORGANISM: Mouse

<400> SEQUENCE: 2

Cys Gly Asn Leu Ser Thr Cys Met Leu Gly Thr Tyr Thr Gln Asp Leu
1               5                   10                  15

Asn Lys Phe His Thr Phe Pro Gln Thr Ser Ile Gly Val Glu Ala Pro
            20                  25                  30

<210> SEQ ID NO 3
<211> LENGTH: 32
<212> TYPE: PRT
<213> ORGANISM: Chicken

<400> SEQUENCE: 3

Cys Ala Ser Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

<210> SEQ ID NO 4
<211> LENGTH: 32
<212> TYPE: PRT
<213> ORGANISM: Eel

<400> SEQUENCE: 4

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

<210> SEQ ID NO 5
<211> LENGTH: 32
<212> TYPE: PRT
<213> ORGANISM: Rat

<400> SEQUENCE: 5

Cys Gly Asn Leu Ser Thr Cys Met Leu Gly Thr Tyr Thr Gln Asp Leu
1               5                   10                  15

Asn Lys Phe His Thr Phe Pro Gln Thr Ser Ile Gly Val Gly Ala Pro
            20                  25                  30

<210> SEQ ID NO 6
<211> LENGTH: 32
<212> TYPE: PRT
<213> ORGANISM: Horse

<400> SEQUENCE: 6

Cys Ser Asn Leu Ser Thr Cys Val Leu Gly Thr Tyr Thr Gln Asp Leu
1               5                   10                  15

Asn Lys Phe His Thr Phe Pro Gln Thr Ala Ile Gly Val Gly Ala Pro
            20                  25                  30

<210> SEQ ID NO 7
<211> LENGTH: 32
<212> TYPE: PRT
<213> ORGANISM: Canine

<400> SEQUENCE: 7

Cys Ser Asn Leu Ser Thr Cys Val Leu Gly Thr Tyr Ser Lys Asp Leu
1               5                   10                  15

Asn Asn Phe His Thr Phe Ser Gly Ile Gly Phe Gly Ala Glu Thr Pro
            20                  25                  30

<210> SEQ ID NO 8
<211> LENGTH: 32
<212> TYPE: PRT
<213> ORGANISM: Canine

<400> SEQUENCE: 8

Cys Ser Asn Leu Ser Thr Cys Val Leu Gly Thr Tyr Thr Gln Asp Leu
1               5                   10                  15

Asn Lys Phe His Thr Phe Pro Gln Thr Ala Ile Gly Val Gly Ala Pro
            20                  25                  30

<210> SEQ ID NO 9
<211> LENGTH: 32
<212> TYPE: PRT
<213> ORGANISM: Porcine

<400> SEQUENCE: 9

Cys Ser Asn Leu Ser Thr Cys Val Leu Ser Ala Tyr Trp Arg Asn Leu
1               5                   10                  15

Asn Asn Phe His Arg Phe Ser Gly Met Gly Phe Gly Pro Glu Thr Pro
            20                  25                  30

<210> SEQ ID NO 10
<211> LENGTH: 32
<212> TYPE: PRT
<213> ORGANISM: Human

<400> SEQUENCE: 10

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: 1..1
<223> OTHER INFORMATION: ACETYLATION
<220> FEATURE:
<221> NAME/KEY: MOD_RES
<222> LOCATION: 32..32
<223> OTHER INFORMATION: AMIDATION

<400> SEQUENCE: 11

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Thr Tyr
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: 1..1
<223> OTHER INFORMATION: ACETYLATION
<220> FEATURE:
<221> NAME/KEY: MOD_RES
<222> LOCATION: 32..32
<223> OTHER INFORMATION: ACETYLATION

<400> SEQUENCE: 12

Cys Ser Asn Leu Ser Thr Cys Val Leu Gly Arg Leu Ser Gln Glu Leu
1               5                   10                  15

His Arg Leu Gln Thr Phe Pro Arg Thr Asp Val Gly Ala Asn Thr Tyr
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: Synthetic Construct
<220> FEATURE:

```
<221> NAME/KEY: MOD_RES
<222> LOCATION: 1..1
<223> OTHER INFORMATION: propionyl
<220> FEATURE:
<221> NAME/KEY: MOD_RES
<222> LOCATION: 32..32
<223> OTHER INFORMATION: AMIDATION

<400> SEQUENCE: 13

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: 1..1
<223> OTHER INFORMATION: Succinyl
<220> FEATURE:
<221> NAME/KEY: MOD_RES
<222> LOCATION: 32..32
<223> OTHER INFORMATION: AMIDATION

<400> SEQUENCE: 14

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic construct
<220> FEATURE:
<221> NAME/KEY: MOD_RES
<222> LOCATION: 1..1
<223> OTHER INFORMATION: ACETYLATION
<220> FEATURE:
<221> NAME/KEY: MOD_RES
<222> LOCATION: 32..32
<223> OTHER INFORMATION: AMIDATION

<400> SEQUENCE: 15

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Ala Pro
            20                  25                  30

<210> SEQ ID NO 16
<211> LENGTH: 33
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: 33..33
<223> OTHER INFORMATION: AMIDATION

<400> SEQUENCE: 16

Lys Cys Ser Asn Leu Ser Thr Cys Val Leu Gly Lys Leu Ser Gln Glu
```

```
1               5                   10                  15
Leu His Lys Leu Gln Thr Tyr Pro Arg Thr Asp Val Gly Ala Asn Thr
            20                  25                  30

Tyr

<210> SEQ ID NO 17
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: 1..1
<223> OTHER INFORMATION: Succinyl
<220> FEATURE:
<221> NAME/KEY: MOD_RES
<222> LOCATION: 32..32
<223> OTHER INFORMATION: AMIDATION

<400> SEQUENCE: 17

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Ala Tyr
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: 1..1
<223> OTHER INFORMATION: Cysteine can be modified with an acetyl group,
      propionyl group, or succinyl group.
<220> FEATURE:
<221> NAME/KEY: SITE
<222> LOCATION: 31..31
<223> OTHER INFORMATION: Xaa can be any naturally occurring amino acid
<220> FEATURE:
<221> NAME/KEY: SITE
<222> LOCATION: 32..32
<223> OTHER INFORMATION: Xaa can be any naturally occurring amino acid
<220> FEATURE:
<221> NAME/KEY: MOD_RES
<222> LOCATION: 32..32
<223> OTHER INFORMATION: Optionally amidated

<400> SEQUENCE: 18

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Xaa Xaa
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: Optional acylation
<220> FEATURE:
<221> NAME/KEY: MOD_RES
<222> LOCATION: 32
<223> OTHER INFORMATION: Amidation
```

<400> SEQUENCE: 19

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Ala Pro
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: Optional acylation
<220> FEATURE:
<221> NAME/KEY: MOD_RES
<222> LOCATION: 32
<223> OTHER INFORMATION: Amidation

<400> SEQUENCE: 20

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: Optional acylation
<220> FEATURE:
<221> NAME/KEY: MOD_RES
<222> LOCATION: 32
<223> OTHER INFORMATION: Amidation

<400> SEQUENCE: 21

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Thr Tyr
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: Optional amidation
<220> FEATURE:
<221> NAME/KEY: MOD_RES
<222> LOCATION: 32
<223> OTHER INFORMATION: Acetylation

<400> SEQUENCE: 22

Cys Ser Asn Leu Ser Thr Cys Val Leu Gly Arg Leu Ser Gln Glu Leu
1               5                   10                  15

His Arg Leu Gln Thr Phe Pro Arg Thr Asp Val Gly Ala Asn Thr Tyr

```
<210> SEQ ID NO 23
<211> LENGTH: 33
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: Optional acylation
<220> FEATURE:
<221> NAME/KEY: MOD_RES
<222> LOCATION: 33
<223> OTHER INFORMATION: Amidation

<400> SEQUENCE: 23

Lys Cys Ser Asn Leu Ser Thr Cys Val Leu Gly Lys Leu Ser Gln Glu
1               5                   10                  15

Leu His Lys Leu Gln Thr Tyr Pro Arg Thr Asp Val Gly Ala Asn Thr
            20                  25                  30

Tyr

<210> SEQ ID NO 24
<211> LENGTH: 32
<212> TYPE: PRT
<213> ORGANISM: Artificial Sequence
<220> FEATURE:
<223> OTHER INFORMATION: Calcitonin mimetic
<220> FEATURE:
<221> NAME/KEY: MOD_RES
<222> LOCATION: 1
<223> OTHER INFORMATION: Optional acylation
<220> FEATURE:
<221> NAME/KEY: MOD_RES
<222> LOCATION: 32
<223> OTHER INFORMATION: Amidation

<400> SEQUENCE: 24

Cys Ser Asn Leu Ser Thr Cys Val Leu Gly Lys Leu Ser Gln Glu Leu
1               5                   10                  15

His Lys Leu Gln Thr Tyr Pro Arg Thr Asp Val Gly Ala Asn Ala Tyr
            20                  25                  30
```